(12) United States Patent
Sullivan

(10) Patent No.: US 8,721,642 B1
(45) Date of Patent: May 13, 2014

(54) TISSUE COOLING CLAMPS AND RELATED METHODS

(71) Applicant: Neuraxis, LLC, Traverse City, MI (US)

(72) Inventor: John Sullivan, Pelham, NH (US)

(73) Assignee: Neuraxis, LLC, Traverse City, MI (US)

( * ) Notice: Subject to any disclaimer, the term of this patent is extended or adjusted under 35 U.S.C. 154(b) by 0 days.

(21) Appl. No.: 13/751,503

(22) Filed: Jan. 28, 2013

(51) Int. Cl.
*A61B 17/80* (2006.01)
*A61B 17/58* (2006.01)
*A61B 17/70* (2006.01)
*A61F 7/00* (2006.01)

(52) U.S. Cl.
USPC ............ 606/60; 606/86 A; 606/86 B; 606/21

(58) Field of Classification Search
USPC .............. 607/96, 83, 87, 104, 105, 107, 112; 165/46; 602/14, 36, 37; 600/20–26; 606/60, 86 R, 277
See application file for complete search history.

(56) References Cited

U.S. PATENT DOCUMENTS

| | | | | |
|---|---|---|---|---|
| 3,369,550 | A | * | 2/1968 | Armao ............................ 606/23 |
| 4,745,922 | A | | 5/1988 | Taylor |
| 4,781,193 | A | | 11/1988 | Pagden |
| 4,784,126 | A | * | 11/1988 | Hourahane ...................... 606/60 |
| 5,108,390 | A | | 4/1992 | Potocky et al. |
| 5,196,015 | A | | 3/1993 | Neubardt |
| 5,433,739 | A | | 7/1995 | Sluijter et al. |
| 5,474,558 | A | | 12/1995 | Neubardt |
| 5,531,776 | A | | 7/1996 | Ward et al. |
| 5,571,147 | A | | 11/1996 | Sluijter et al. |
| 5,616,143 | A | * | 4/1997 | Schlapfer et al. ........... 606/86 A |
| 5,693,099 | A | | 12/1997 | Harle |
| 5,899,898 | A | | 5/1999 | Arless et al. |
| 6,343,644 | B1 | | 2/2002 | Huang et al. |
| 6,613,044 | B2 | | 9/2003 | Carl |
| 6,629,975 | B1 | * | 10/2003 | Kilpela et al. .................. 606/60 |

(Continued)

FOREIGN PATENT DOCUMENTS

| | | |
|---|---|---|
| RU | 1727802 | 4/1992 |
| WO | 2009103758 A2 | 8/2009 |

OTHER PUBLICATIONS

[No Author Listed] Thermally Conductive Polymers—CoolPoly Thermally Conductive Plastics. Cool Polymers. 2013. http://www.coolpolymers.com/. 1 page. Last Accessed Feb. 20, 2013.

(Continued)

*Primary Examiner* — Michael Peffley
(74) *Attorney, Agent, or Firm* — Nutter McClennen & Fish LLP

(57) ABSTRACT

Methods and devices are disclosed herein that generally involve cooling tissue (e.g., localized cooling of tissue), and in particular applying therapeutic hypothermia to the spinal canal, tissue disposed within the spinal canal, and/or nerve roots extending from the spinal canal. In some embodiments, tissue can be cooled by clamping a cooling instrument to a bone or implant that is proximate to the tissue. The cooling instrument can define a chamber through which a chilled fluid, expandable gas, or other coolant means can be circulated, delivered, or activated to cool adjacent tissue. The degree of cooling can be regulated using a controller, which can be configured to increase or decrease the cooling effect based on any of a variety of measured or predicted physiological or thermodynamic properties. Methods are disclosed for utilizing cooling instruments and for carrying out various treatment regimens that involve cooling tissue using such instruments.

15 Claims, 13 Drawing Sheets

(56) References Cited

U.S. PATENT DOCUMENTS

| | | | |
|---|---|---|---|
| 6,699,240 B2* | 3/2004 | Francischelli | 606/32 |
| 6,749,605 B2 | 6/2004 | Ashley et al. | |
| 6,796,985 B2 | 9/2004 | Bolger et al. | |
| 6,818,011 B2 | 11/2004 | Dobak, III | |
| 6,899,694 B2* | 5/2005 | Kadziauskas et al. | 604/35 |
| 7,144,394 B2 | 12/2006 | Carl | |
| 7,220,951 B2* | 5/2007 | Truckai et al. | 219/770 |
| 7,241,297 B2 | 7/2007 | Shaolian et al. | |
| 7,347,856 B2* | 3/2008 | Wittenberger et al. | 606/23 |
| 7,449,019 B2 | 11/2008 | Uchida et al. | |
| 7,645,282 B2* | 1/2010 | Huxel et al. | 606/103 |
| 7,651,496 B2* | 1/2010 | Keegan et al. | 606/60 |
| 7,722,620 B2 | 5/2010 | Truckai et al. | |
| 7,819,860 B2* | 10/2010 | Wittenberger et al. | 606/23 |
| 8,348,952 B2 | 1/2013 | Sanders et al. | |
| 8,523,930 B2 | 9/2013 | Saunders et al. | |
| 2002/0095144 A1 | 7/2002 | Carl | |
| 2003/0018331 A1* | 1/2003 | Dycus et al. | 606/48 |
| 2003/0216721 A1 | 11/2003 | Diederich et al. | |
| 2004/0102825 A1 | 5/2004 | Daoud | |
| 2004/0210286 A1 | 10/2004 | Saadat | |
| 2005/0149007 A1 | 7/2005 | Carl | |
| 2006/0015160 A1 | 1/2006 | Larnard | |
| 2006/0241576 A1 | 10/2006 | Diederich et al. | |
| 2007/0050002 A1* | 3/2007 | Elefteriades | 607/105 |
| 2007/0162007 A1 | 7/2007 | Shoham | |
| 2007/0191831 A1 | 8/2007 | Sanders et al. | |
| 2007/0225781 A1 | 9/2007 | Saadat et al. | |
| 2007/0233148 A1 | 10/2007 | Truckai et al. | |
| 2007/0233226 A1 | 10/2007 | Kochamba et al. | |
| 2007/0233249 A1 | 10/2007 | Shadduck | |
| 2007/0260232 A1 | 11/2007 | Carl | |
| 2007/0260250 A1 | 11/2007 | Wisnewski et al. | |
| 2008/0065062 A1 | 3/2008 | Leung et al. | |
| 2008/0065083 A1 | 3/2008 | Truckai et al. | |
| 2008/0154373 A1 | 6/2008 | Protopsaltis et al. | |
| 2008/0249532 A1* | 10/2008 | Schoutens et al. | 606/99 |
| 2008/0269761 A1 | 10/2008 | Truckai et al. | |
| 2008/0294222 A1* | 11/2008 | Schechter | 607/50 |
| 2009/0036893 A1* | 2/2009 | Kartalian et al. | 606/60 |
| 2011/0066216 A1* | 3/2011 | Ting et al. | 607/104 |
| 2011/0282418 A1 | 11/2011 | Saunders et al. | |
| 2012/0065733 A1 | 3/2012 | Wieder | |
| 2012/0221059 A1* | 8/2012 | Mollman et al. | 606/277 |

OTHER PUBLICATIONS

[No Author Listed] Gap Pad Products—Thermal Materials, Thermal Solutions. The Bergquist Company. 2013. http://www.bergquistcompany.com/thermal_materials/gap-pad.htm. 2 pages. Last Accessed Feb. 20, 2013.

[No Author Listed] BioMedical. Tullurex. 2013. http://www.tellurex.com/markets/biomedical.php. 2 pages. Last Accessed Feb. 20, 2013.

International Search Report and Written Opinion, PCT/US2011/036436, dated Feb. 9, 2012 (11 Pages).

* cited by examiner

US 8,721,642 B1

TISSUE COOLING CLAMPS AND RELATED METHODS

FIELD

The present invention relates to methods and devices for cooling tissue. In some embodiments, clamps for cooling spinal tissue and related methods are provided.

BACKGROUND

According to the National Spinal Cord Injury Statistical Center, there are more than 259,000 people living with a spinal cord injury in the United States. Traumatic spinal cord injury afflicts around 15,000 people in the United States each year. Approximately 12,000 survive the cord injury with a neurological deficit, which is commonly a severe, disabling physical impairment and mental burden. Long-term care for cord injuries costs an estimated $9.7 billion annually in the United States.

Application of certain degrees of hypothermia to a patient's spine and spinal cord after a spinal cord injury can lead to benefits, such as a reduction of the metabolic demand of spinal cord cells, reduction of edema, added tolerance to hypoxia/ischemia, and ultimately a reduction in spinal cord tissue damage or cell death. Realizing these benefits could mean the difference between quadriplegia and being able to use one's arms. The use of a cooling effect for these purposes can be referred to as therapeutic hypothermia.

Besides traumatic spinal cord injury, the spinal cord can be injured due to surgical procedures such as abdominal aneurysm repair, wherein blood flow to the spinal cord is reduced. This lack of blood flow, also known as ischemia, can cause cellular damage to the spinal cord. Local cooling of the spinal cord can decrease the incidence of spinal cord injury in abdominal aneurysm surgery. Nerve roots or any member of the central nervous system in the spine can also become damaged from trauma and/or surgical insult, and can cause neurologic deficits and/or significant patient pain. It will be appreciated that the spinal cord and nerves can become injured through any number of means.

Existing methods for cooling the spine involve systemic cooling of the entire body. Such treatments carry a number of disadvantages. For one thing, systemic cooling techniques lack the ability to specifically target the injured tissue and, as a result, other unrelated tissue can be damaged or destroyed by the cooling. Systemic cooling can also cause a wide variety of side effects. In addition, the degree to which the body can be cooled systemically is very limited, and it is difficult to precisely control the degree to which the body is cooled in systemic approaches. Body temperature changes using systemic techniques also tend to occur very slowly, which can undesirably delay administration of a cooling effect to the injured tissue. Accordingly, a need exists for improved methods and devices for cooling tissue.

SUMMARY

Methods and devices are disclosed herein that generally involve cooling tissue (e.g., localized cooling of tissue), and in particular applying therapeutic hypothermia to the spinal canal, tissue disposed within the spinal canal, and/or nerve roots extending from the spinal canal. In some embodiments, tissue can be cooled by clamping a cooling instrument to a bone or implant that is proximate to the tissue. The cooling instrument can define a chamber through which a chilled fluid, expandable gas, or other coolant means can be circulated, delivered, or activated to cool adjacent tissue. The degree of cooling can be regulated using a controller, which can be configured to increase or decrease the cooling effect based on any of a variety of measured or predicted physiological or thermodynamic properties. Methods are disclosed for utilizing cooling instruments and for carrying out various treatment regimens that involve cooling tissue using such instruments.

In some embodiments, a tissue cooling device is provided that includes a clamp configured to grasp at least one of a bony structure of a vertebra and an implant, the clamp having a heat exchange surface, and a cooling mechanism in thermal communication with the clamp such that a cooling effect can be applied through the heat exchange surface to a bony structure or implant grasped by the clamp. In one embodiment, the clamp can include a thermally-insulating surface, e.g., to prevent cooling of unintended anatomy. The clamp can be configured to grasp any of a variety of implants, including, e.g., at least one of a bone screw, a bone hook, a connecting rod, a percutaneous access device, a spinal plate, a disk replacement implant, and an interspinous process plate. The bony structure can be, for example, at least one of a transverse process, a lamina, a pedicle, and a spinous process.

A variety of cooling mechanisms can be provided. For example, the cooling mechanism can include a thermoelectric cooler. Alternatively, or in addition, the cooling mechanism can include a cooling fluid delivery conduit, a cooling fluid exhaust conduit, and a cooling fluid chamber in fluid communication with the delivery conduit and the exhaust conduit and in thermal communication with the heat exchange surface of the clamp. The clamp can have various configurations. In some embodiments, the clamp can include first and second movable jaws. The jaws can be configured to substantially surround at least a portion of an implant, e.g., the head of a pedicle screw. The heat exchange surface can include toothed gripping surfaces of the first and second movable jaws. In some embodiments, the cooling mechanism can be at least partially disposed within the first jaw. The device can include various additional components, including without limitation a biasing element configured to bias the jaws toward a closed position, a locking mechanism configured to lock the jaws in a particular position relative to one another, and/or a tightening screw configured to advance the jaws towards one another.

In some embodiments, the clamp can include an adapter that conforms to the bony structure or implant in an interference fit. The adapter can be formed from a variety of materials, including conformable materials. A variety of cooling mechanisms can be provided. For example, the cooling mechanism can include a thermoelectric cooler disposed between the adapter and a heat sink. By way of further example, the cooling mechanism can include a thermally-conductive, polymeric boot portion and a metallic head portion in which the cooling mechanism is disposed. In some embodiments, the clamp can include a collet disposable over the bony structure or implant and the cooling mechanism can be configured to fit over the collet and compress the collet against the bony structure or implant. In some embodiments, the clamp can include an expandable member disposable within a recess formed in the bony structure or implant and a tightening nut matable to the expandable member such that rotation of the nut relative to the expandable member causes a wedge portion of the nut to expand the expandable member into engagement with the recess.

In some embodiments, a method for cooling tissue is provided that includes engaging at least one of a bony structure of a vertebra and an implant with a clamp, and applying a cooling effect to the clamp to cool the bony structure or implant and nerve tissue adjacent thereto.

The method can include preparing the bony structure to receive the clamp. The method can include engaging a plurality of bony structures or a plurality of implants with a plurality of clamps, and applying a cooling effect to the plurality of clamps to cool the plurality of bony structures or the plurality of implants and nerve tissue adjacent thereto. Engaging at least one of a bony structure of a vertebra and an implant can include attaching the clamp directly to at least one of a pedicle, a posterior arch, a spinous process, and a transverse process. Applying the cooling effect can include delivering a pressurized gas to a chamber formed within the clamp. Applying the cooling effect can include delivering a cooled liquid to a chamber formed within the clamp and withdrawing the cooled liquid from the chamber through an exhaust conduit. The method can include dynamically controlling the cooling effect to increase and decrease the cooling effect. The method can include, prior to or during said controlling, measuring one or more measured physiological characteristics using a sensor.

The present invention further provides methods, systems, and devices as claimed.

BRIEF DESCRIPTION OF THE DRAWINGS

The invention will be more fully understood from the following detailed description taken in conjunction with the accompanying drawings, in which.

DETAILED DESCRIPTION

Methods and devices are disclosed herein that generally involve cooling tissue (e.g., localized cooling of tissue), and in particular applying therapeutic hypothermia to the spinal canal, tissue disposed within the spinal canal, and/or nerve roots extending from the spinal canal. In some embodiments, tissue can be cooled by clamping a cooling instrument to a bone or implant that is proximate to the tissue. The cooling instrument can define a chamber through which a chilled fluid, expandable gas, or other coolant means can be circulated, delivered, or activated to cool adjacent tissue. The degree of cooling can be regulated using a controller, which can be configured to increase or decrease the cooling effect based on any of a variety of measured or predicted physiological or thermodynamic properties. Methods are disclosed for utilizing cooling instruments and for carrying out various treatment regimens that involve cooling tissue using such instruments.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

In the description that follows, reference is made primarily to cooling tissue in and around the spinal canal, including the spinal cord, but it will be appreciated that the methods and devices disclosed herein can also be used to cool tissue in virtually any part of a human or animal body, including organs, joints (e.g., hips, knees, elbows, shoulders), the brain, the heart, etc. It will also be appreciated that the term "spinal tissue" as used herein can include the spinal cord itself, as well as nerves and nerve roots extending therefrom through spaces in the spinal column, together the "spinal neuraxis," as well as other portions of the central nervous system.

System Generally

Figure 1:
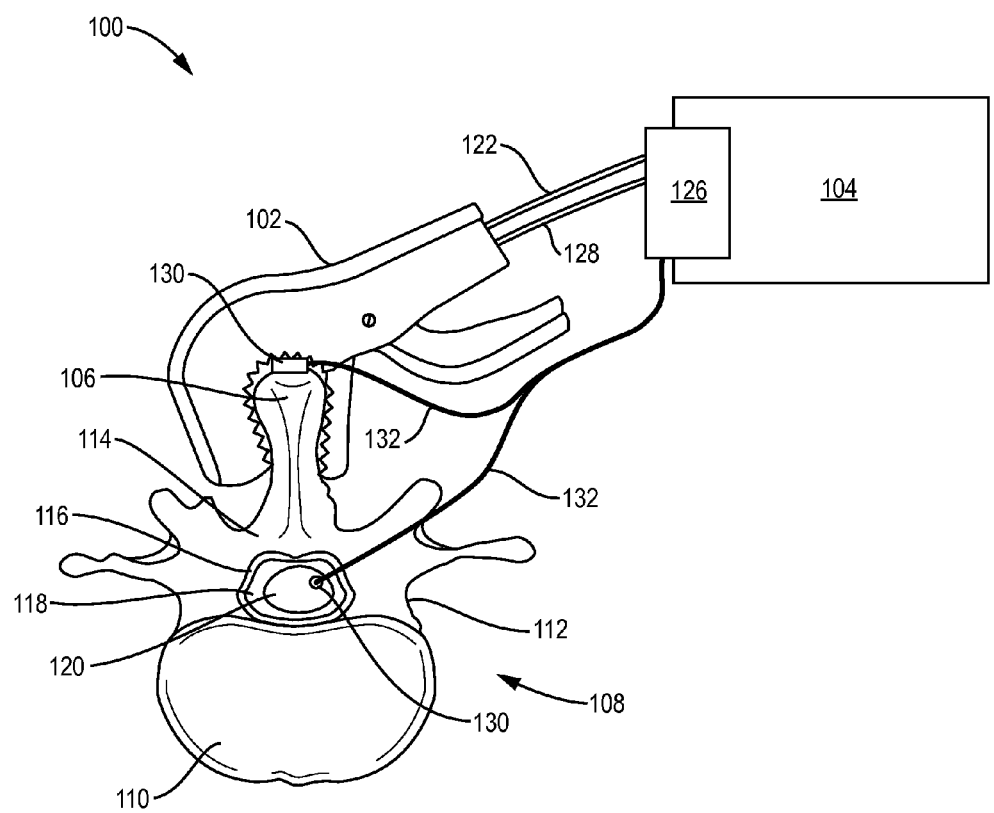
FIG. 1 is a schematic view of a cooling instrument coupled to a vertebra.

FIG. 1A illustrates an exemplary embodiment of a system 100 for cooling tissue. The system 100 generally includes a cooling instrument 102 and a source 104 configured to provide a coolant means to the instrument 102. The cooling instrument 102 can be a clamp that is configured to attach to a portion of the patient's anatomy. The clamp can be attached directly to an anatomical structure, or it can be attached indirectly thereto (e.g., via one or more intermediate implants or other structures).

In the illustrated embodiment, the cooling instrument 102 is clamped directly to the spinous process 106 of a vertebra 108. The cooling instrument 102 can also be attached to other portions of the vertebra, such as the vertebral body 110, the pedicles 112, or the laminae 114. By applying a cooling effect to a portion of the vertebra 108, the spinal canal 116, and the spinal canal contents 118, including the spinal cord 120, can be cooled. The spinal canal contents 118 include, for example, epidural space, dura mater, subdural space, arachnoid space, subarachnoid space, intrathecal space, cerebral spinal fluid, pia mater, spinal arteries and veins, vasocorona, vertebral venous plexus, nerve roots, ligaments, and fatty tissue. It will be appreciated that there is symmetry as well as repetitive elements to a vertebra and referral to an element of the vertebra can be taken to mean any one of symmetric or multiple elements. For example, when referring to a pedicle, it can be intended to mean any one of the two, or both, pedicles of the vertebra.

Coolant Means and Source

The cooling instrument 102 can provide a cooling effect using any of a number of different coolant means or combinations thereof. For example, the coolant means can include the expansion of gas within the cooling instrument 102 or the circulating of a chilled fluid through the cooling instrument 102. The term "fluid," as used herein, refers to any flowable material or collection of materials, including liquids, gasses, and combinations thereof. In one embodiment, the cooling instrument 102 receives a compressed gas which by expansion acts as a coolant in the cooling instrument 102. The expansion of the gas causes the gas and the cooling instrument 102 around it to experience a rapid decrease in temperature. Typical gases for such an application include Nitrous Oxide and Carbon Dioxide, but it will be appreciated that there are a wide variety of gases that can be used, including gasses which, in compressed form, will be liquid.

In other embodiments, the cooling instrument 102 receives a chilled liquid as the coolant means which flows through cavities or channels of the cooling instrument, thereby decreasing the temperature of the cooling instrument. Typical chilled liquids include saline solutions, water, liquid nitrogen, and ethyl alcohol. It will be appreciated that any number of fluids can be used as the coolant means, and that there are advantages to using biologically safe fluids. In still other embodiments, the cooling instrument 102 can include a thermoelectric device, such as a Peltier device, which when a voltage or current is applied, at least a portion of the device experiences a reduction in temperature. The cooling instrument 102 can also house an endothermic chemical reaction which results in the reduction of temperature of the contents of the cooling instrument 102 and of the cooling instrument 102 itself. In other embodiments, the cooling instrument 102 is pre-chilled prior to a cooling procedure. It will be appreciated by those skilled in the art that there are a variety of means by which the cooling instrument 102 can be cooled.

The coolant source 104 can be external (e.g., extracorporeal), can be implanted in the patient, and/or can be formed integrally with the cooling instrument 102. In implementations in which the coolant means is an expanding gas, the coolant source 104 can be a tank of compressed gas which is released into the cooling instrument 102 through a coolant delivery conduit 122. Once the compressed gas is in the cooling instrument 102, it can be expanded through an expansion nozzle into an expansion chamber 124 (shown in FIG. 2A) in the cooling instrument 102, causing a rapid decrease in temperature. Alternatively, or in addition, the coolant source 104 can include a compressor that compresses the gas. In some implementations, the delivery of the coolant means from the tank of compressed gas is regulated with a control unit 126 to limit the amount of gas and the pressure at which it enters the cooling instrument 102 via the coolant delivery conduit 122. The control unit 126 can be an adjustable valve on the tank, which can be manually controlled, mechanically controlled, or automatically controlled by a computing device. In implementations in which the coolant source 104 includes a compressor, the control unit 126 can control the degree to which the compressor compresses the gas, or the pressure of the gas presented down the conduit 122. The regulation of the release of the gas can be managed manually or automatically, in either case, based on established protocols, conditions of the patient, and/or detectable physiological characteristics of the patient or characteristics of the cooling instrument.

An additional conduit 128 can also be provided to exhaust expanded gas from the expansion chamber 124 of the cooling instrument 102. The exhaust conduit 128 can exhaust the gas into the atmosphere, to a collection tank, or to a compressor which in turn re-compresses the gas for reuse. The delivery conduit 122 and the exhaust conduit 128 can be generally circular in cross-section, and can be formed from any of a variety of medical-grade tubing materials known in the art. The conduits 122, 128 can be flexible or rigid, or can include rigid portions and flexible portions.

In implementations in which the coolant means is a chilled fluid, the coolant source 104 can be or can include a chiller or other apparatus for cooling and pumping fluid, and the coolant delivery conduit 122 can be a tube for delivering the chilled fluid to the cooling instrument 102. In this case, the exhaust conduit 128 can be used to return or exhaust the chilled fluid from the cooling instrument 102 back to the coolant source 104, to a collection tank, or to a drain. In such an implementation, the control unit 126 can control the volume rate of chilled fluid flow, the pressure of the chilled fluid delivery lines, and/or the temperature of the chilled fluid. It will be appreciated that components of the fluid delivery and circulation system can be positioned on the exhaust side of the system rather than the source side (e.g., a pumping mechanism that pulls the chilled fluid through the instrument 102, the delivery conduit 122, and the exhaust conduit 128 rather than pushing it through).

In implementations in which the coolant means is a Peltier device embedded in the cooling instrument 102, the coolant source 104 can include a power supply that powers the Peltier device, and the coolant delivery conduit 122 can include electrical lines that supply electrical current from the power supply to the Peltier device. The delivery and exhaust conduits 122, 128 can also be used to remove heat generated by the Peltier device from the cooling instrument 102.

Delivery of the coolant means can be regulated to achieve a predetermined cooling effect, such as a specific temperature at a specific location. Delivery of the coolant means can also be regulated such that a specific volume of the coolant means is delivered, for example in cases where the coolant means includes a chilled liquid or expandable gas. Delivery of the coolant means can also be regulated based on changes or lack of changes in physiological characteristics. For example, the regulation of the coolant means, and thus the intensity of cooling, can be determined by quantitative and qualitative sensory or motor-evoked potential (SEP, MEP) observations. In this example, the coolant means is provided at a certain level until the patient's SEP/MEP results begin to degrade, improve, or otherwise change, at which point the regulation of the coolant means can begin to reduce or increase the delivery of the coolant means.

It will be appreciated that any number of physiological characteristics can be used to regulate the intensity of the coolant means, including but not limited to: blood pressure, target-tissue temperature, specific tissue temperature (proximate to target tissue), rectal body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, and effectors of excitotoxicity, vasogenic edema, apoptosis, inflammation, and enzymatic responses. A real-time qualitative or quantitative determination can be made based on any of the listed physiological characteristics as to how the coolant means should be regulated.

One or more sensors 130 can also be included in the cooling instrument 102 and/or implanted in or around the patient. The sensor 130 can be a temperature sensor embedded in or on the cooling instrument 102 to sense the temperature the instrument exhibits, where this sensed temperature can then be used to control the delivery of the coolant means to the cooling instrument 102. The sensor 130 can be connected to the control unit 126 via one or more sensor wires 132 to provide a feedback loop of information to help determine how much coolant means and/or what temperature coolant means to deliver to the cooling instrument 102. Alternatively, or in addition, the sensor 130 can be connected via sensor wires to a display, meter, dial, or other indicator providing some form of output data from the sensor 130 that can allow one to manually regulate the delivery of the coolant means. The sensor 130 can also be connectable wirelessly and a wireless link can be used instead of the sensor wires 132.

In one implementation, a first sensor 130 is embedded into the cooling instrument 102 and provides temperature data of the cooling instrument 102 and a second sensor 130 is implanted in the intrathecal space of the spinal canal 116 to measure temperature of cerebral spinal fluid. This temperature data can be used to either manually or automatically regulate the delivery of the coolant means.

It will be appreciated that more than one sensor 130, more than one sensor type, and more than one sensor placement location can be used simultaneously and that the data gathered from the multiple sensors 130 can be used independently or in combination to determine how the delivery of the coolant means is regulated. Exemplary sensors that can be used include temperature sensors (e.g., thermistors or thermocouples), pressure sensors, chemical sensors, electrical sensors, magnetic sensors, and optical sensors. Other types of sensing, such as remote sensing, can be used that do not require the sensor itself to be placed within the patient—ultrasound, including Doppler measurements, and functional MRI, all can be used to sense physiological characteristics that can be used to control or regulate the delivery of the coolant means. The information measured by a sensor or sensors can be used to continually adjust the regulation of the delivery of the coolant means in real time or almost real time. Alternatively, or in addition, the sensed information can be used for safety monitoring. The advantages of using a sensor or sensors, along with sensor wires or other communication means, will be appreciated though their use may not be necessary.

Cooling Instruments

Figure 2A:
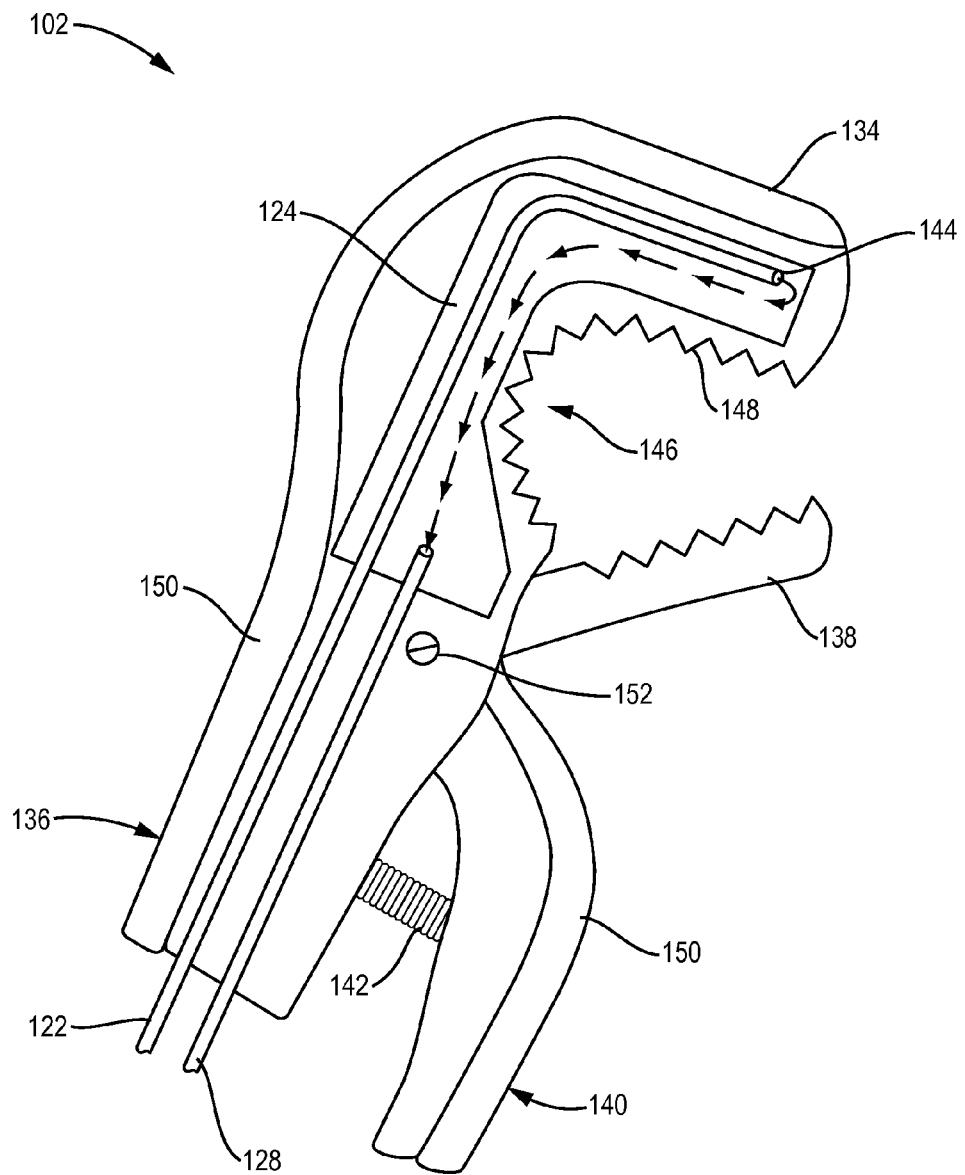
FIG. 2A is a cross-sectional view of an exemplary cooling instrument.

The cooling instrument 102 is shown in more detail in FIG. 2A. As shown, the instrument 102 is generally in the form of a clamp configured to grasp an anatomical structure (e.g., a bony structure of vertebra, such as a transverse process, a spinous process, an articular process, a lamina, a pedicle, or a vertebral body) or an implant (e.g., a bone screw, a bone hook, a disk replacement implant, an interspinous process plate or spacer, a connecting rod, or a bone plate). The clamp can include a fixed jaw 134 coupled to a fixed handle portion 136 and a movable jaw 138 coupled to a movable handle portion 140. It will be appreciated that, in some embodiments, both of the jaws can be movable (e.g., relative to each other and/or relative to one or more handle portions of the instrument). In operation, squeezing the movable handle portion 140 towards the fixed handle portion 136 can be effective to open the jaws (i.e., to move the movable jaw 138 away from the fixed jaw 134). Likewise, moving the movable handle portion 140 away from the fixed handle portion 136 can be effective to close the jaws (i.e., to move the movable jaw 138 towards the fixed jaw 134). As shown, a biasing element 142 (e.g., a coil spring or a leaf spring) can be provided to bias the jaws 134, 138 towards a closed or clamped position, such that a clamping force is continually applied to an object grasped by the jaws, even after a user releases manual pressure from the instrument 102.

As noted above, the instrument 102 can include a cooling chamber 124. The chamber can be formed in the fixed jaw 134 as shown, or the chamber 124 can be formed in the movable jaw 138. In some embodiments, both the fixed jaw 134 and the movable jaw 138 can each include a chamber formed therein. It will be appreciated that the cooling instrument 102 can include any number of jaws, and each jaw may or may not include a cooling chamber formed therein. The chamber 124 can house at least a portion of the elements, volumes, nozzles, fluid lumens, channels, paths, and so forth needed to support the coolant means. In implementations in which the coolant means includes expanding gas, the cooling instrument 102 can include an expansion nozzle 144 through which gas that has entered the cooling instrument 102 via the coolant delivery conduit 122 expands. The gas is expanded into the chamber 124, from which it can be exhausted from the cooling instrument 102 via the exhaust conduit 128. The expanded gas can be exhausted into the environment, into a chamber or tank, or into a compressor which re-compresses it. The flow of the gas is depicted in FIG. 2A by the arrows contained within the elements of the figure. In particular, the arrows show that the gas expands in and through the expansion chamber 124.

In implementations in which the coolant means is a chilled fluid, the fluid can be passed through the chamber 124 of the cooling instrument 102 to deliver a cooling effect thereto and to surrounding tissue. In some embodiments, the chamber 124 can be in the form of a fluid lumen having a first end coupled to the delivery conduit 122 and a second end coupled to the exhaust conduit 128. The chamber/fluid lumen 124 can optionally be coiled, snaked, or formed in some other tortuous, surface-area maximizing shape such that heat exchange to/from fluid that is directed through the chamber 124 can be optimized. The fluid can also simply enter the chamber 124 through the delivery conduit 122, reverse direction, and exit the cooling instrument 102 through the exhaust conduit 128.

In implementations in which the coolant means is a Peltier device, the Peltier device can be embedded inside cooling instrument 102 and electrical lines can be connected to the Peltier device internal to the cooling instrument 102. These electrical lines can extend from the cooling instrument 102 to a power source and optionally a regulator of the cooling effect, which can regulate the voltage or current on the electrical lines. In one embodiment, the power source and/or regulator can be disposed on or in the cooling instrument 102 or in a separate implantable unit.

The cooling instrument 102 can optionally include a plurality of thermal fins formed within the chamber 124. For example, the thermal fins can extend radially inward from an outer wall of the chamber 124. In use, an expanded gas or chilled fluid can circulate around and across the thermal fins, which can improve the thermal conduction from the coolant means to the cooling instrument 102, and thus to the target tissue. The thermal fins can also improve the mechanical strength of the cooling instrument 102. It will be appreciated that the thermal fins can be oriented in a variety of directions, can be spiraling, and can take on a variety of shapes and sizes.

The delivery conduit 122 can extend well into the chamber 124, terminating at a location adjacent to the distal end of the chamber 124. The exhaust conduit 128, on the other hand, can terminate only a small distance into the chamber 124, adjacent to the proximal end thereof. With this relative positioning of the conduit outlets, fluid introduced through the delivery conduit 122 must flow through substantially the entire length of the chamber 124 before being removed through the exhaust conduit 128. In this manner, the thermal transfer between the fluid and the cooling instrument 102 can be maximized and more evenly distributed along the heat exchanging surfaces of the cooling instrument 102. In some embodiments, the chamber 124 and/or the delivery conduit 122 can extend only along discrete portions of the instrument 102 where cooling is desired.

In some embodiments, the delivery conduit 122 can be helically wound around the perimeter of the chamber 124 or across the heat exchange surfaces of the instrument 102. This can advantageously improve thermal transfer between the delivery conduit 122 and the cooling instrument 102. In addition, the delivery conduit 122 can act as an internal baffle, routing fluid released from the distal end of the delivery conduit 122 along a helical path back towards the exhaust conduit 128. Thus, thermal transfer can also be improved between fluid released from the delivery conduit 122 and the cooling instrument 102.

The jaws 134, 138 can define heat exchange surfaces 146 through which thermal energy can be transferred to or from an object that is grasped by the clamp 102. The heat exchange surfaces 146 can be serrated, milled, toothed, or have other surface features 148 to enhance the gripping strength of the instrument 102 and increase the contact surface area between the instrument and an object to which it is attached. The heat exchange or gripping surfaces 146 of the jaws 134, 138 can be sized, shaped, or otherwise configured to grasp a particular portion of a patient's anatomy or a particular type of implant. For example, the heat exchange surface or surfaces can be formed substantially as a negative of corresponding surfaces of a spinous process or other anatomical structure. The heat exchange surfaces 146 can also be formed from a conformable or malleable material configured to substantially conform to the shape of an object being grasped by the jaws 134, 138.

Portions of the cooling instrument 102 other than the heat exchange surfaces 146 can be coated with a thermally insulating material 150, such that the cooling effect is focused at the heat exchange surfaces 146, such that surrounding tissue is protected from the cooling effect, and such that a surgeon or other user holding the instrument is protected from the cooling effect. Exemplary thermally insulating materials include silicone, which can be spray coated onto the instrument 102.

Figure 2B:
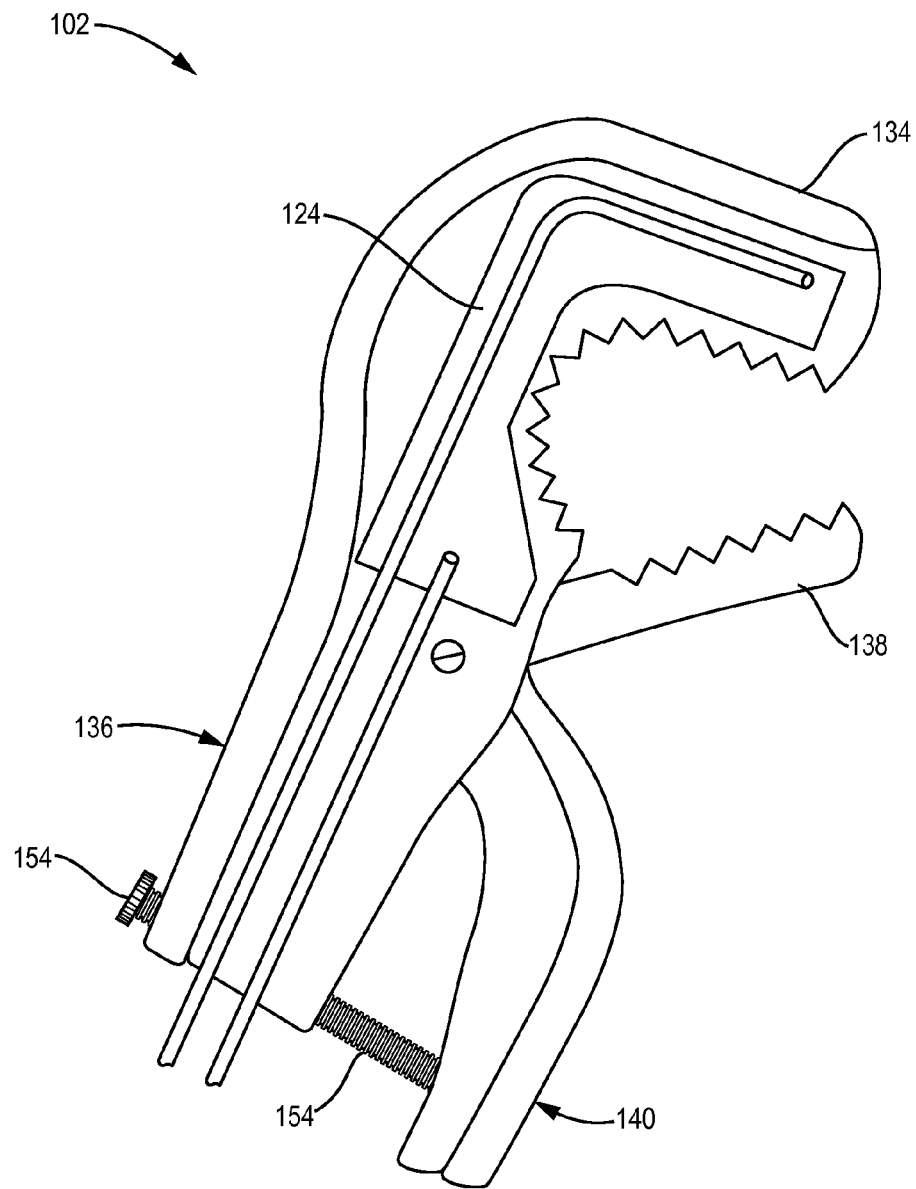
FIG. 2B is a cross-sectional view of another exemplary cooling instrument.

The instrument 102 can include a locking mechanism configured to lock the position of the movable jaw 138 relative to the fixed jaw 134. For example, a set screw 152 can be provided at the pivot pin by which the movable jaw 138 is coupled to the fixed jaw 134, and can be configured such that tightening the set screw 152 locks the jaws relative to one another and loosening the set screw 152 unlocks the jaws. Any of a variety of alternative locking mechanisms known in the art can also be used. As shown in FIG. 2B, the instrument can include an adjustment screw 154. Rotation of the screw 154 in a first direction can cause the movable handle 140 to move towards the fixed handle 136, thereby opening the jaws 134, 138. Rotation of the screw 154 in a second direction opposite to the first direction can cause the movable handle 140 to move away from the fixed handle 136, thereby closing the jaws 134, 138. The adjustment screw 154 can also be configured to lock the relative position of the handles, and therefore the jaws coupled thereto.

Figure 3A:
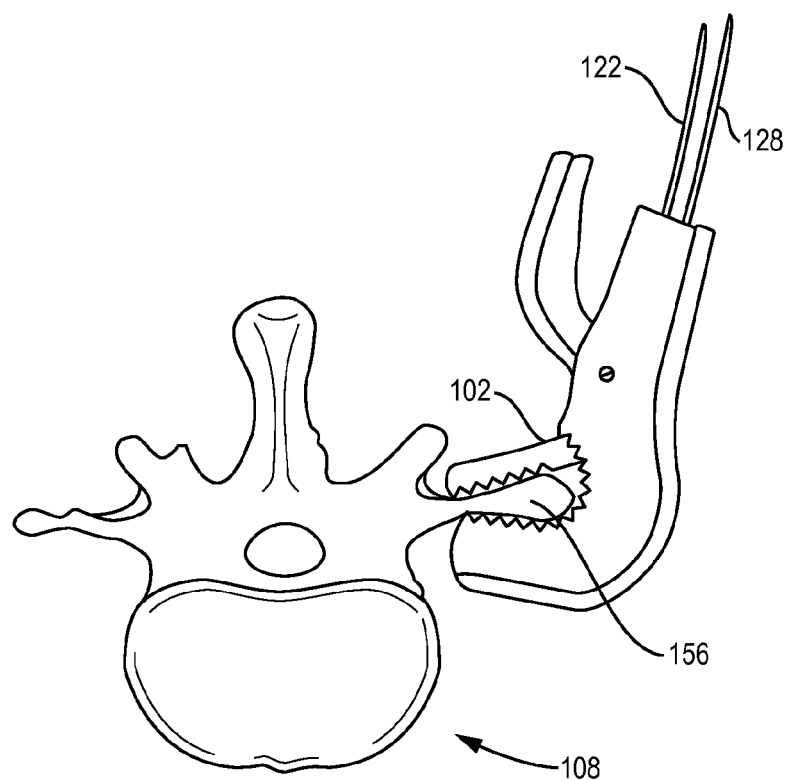
FIG. 3A is a schematic view of a cooling instrument coupled to the transverse process of a vertebra.
Figure 3B:
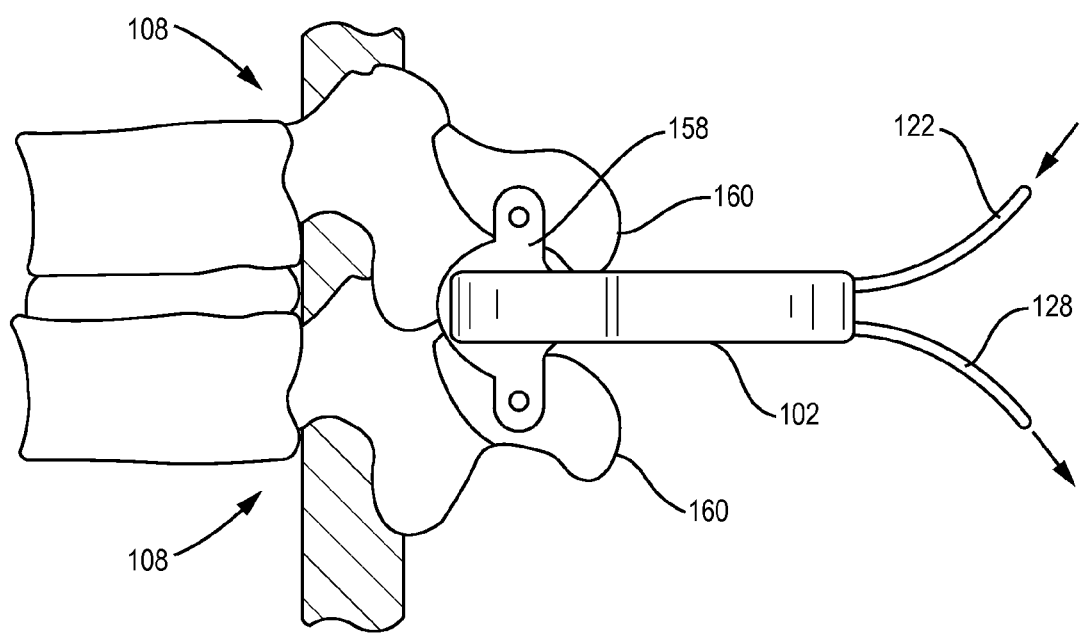
FIG. 3B is a schematic view of a cooling instrument coupled to an interspinous process plate.
Figure 3C:
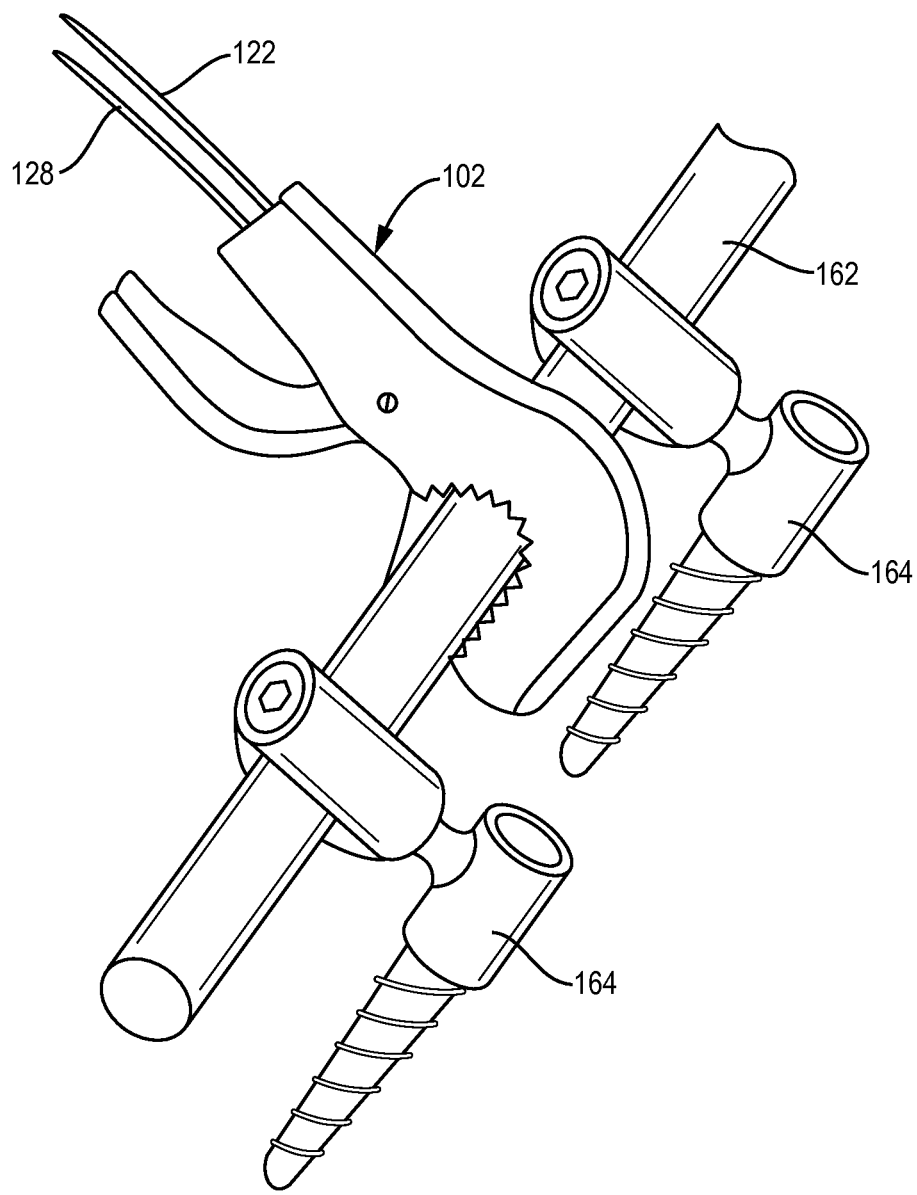
FIG. 3C is a schematic view of a cooling instrument coupled to a spinal connecting rod.

It will be appreciated that the cooling instrument 102 can be coupled to any of a variety of anatomical structures or to any of a variety of implants. As shown in FIG. 3A, the cooling instrument 102 can be configured to couple to a transverse process 156 of a vertebra 108. As shown in FIG. 3B, the cooling instrument 102 can be configured to couple to an interspinous process plate or spacer 158 disposed between the spinous processes 160 of adjacent vertebrae 108. As shown in FIG. 3C, the cooling instrument 102 can be configured to couple to a connecting rod 162, which in turn is coupled to first and second bone screws 164 implanted in one or more vertebrae of the patient. The cooling instrument 102 can also be clamped directly to the bone screws 164 (e.g., to the threaded shank of a bone screw, to the neck of a bone screw, to the head of a bone screw, or to a rod-receiving member coupled to a bone screw).

Figure 4A:
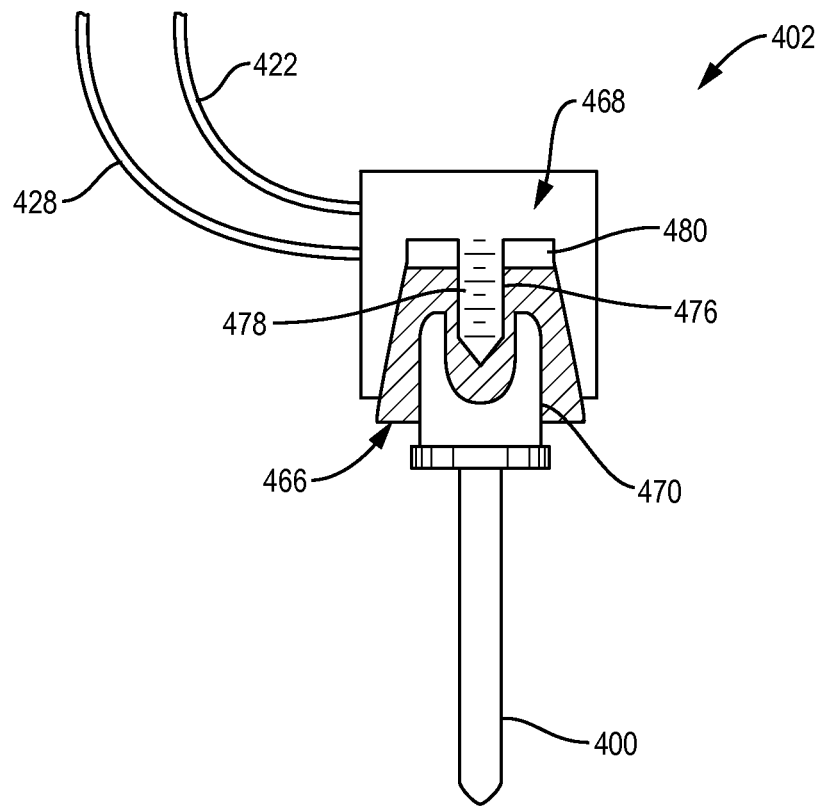
FIG. 4A is a cross-sectional view of another exemplary cooling instrument coupled to a bone screw.
Figure 4B:
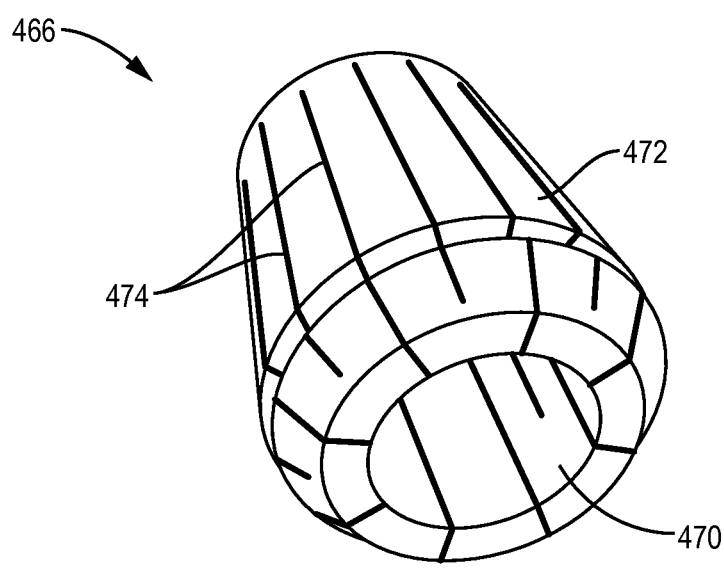
FIG. 4B is a perspective view of a collet portion of the cooling instrument of FIG. 4A.

FIG. 4A illustrates another exemplary embodiment of a cooling instrument or clamp 402. The instrument 402 includes a collet portion 466 and a sleeve portion 468 and is configured to be coupled to an implant 400 (e.g., a rod-receiving head of a bone screw or a rod-receiving member coupled to a bone screw) or to at least a portion of a bone or other anatomical structure. The collet portion 466, shown in detail in FIG. 4B, includes a distal recess 470 sized and shaped to receive a portion of the implant 400 or bone therein (e.g., the rod-receiving portion of a bone screw or other connecting assembly). The collet portion 466 also includes a conical outer surface 472 with a plurality of longitudinal kerf cuts 474 formed therein. The collet portion 466 can be formed from spring steel or other similar materials such that the collet portion can be compressed into firm engagement with the implant 400. The collet portion 466 can also include a threaded proximal recess 476 configured to receive a corresponding threaded internal shaft 478 of the sleeve portion 468. The sleeve portion 468 can include a conical recess 480 sized and shaped to receive the collet portion 466 therein.

In use, the sleeve 468 can be positioned over the collet 466 such that the internal shaft 478 of the sleeve is aligned with the threaded recess 476 of the collet. The sleeve 468 can then be rotated such that it is drawn down over the collet 466, compressing the collet into firm engagement with the implant 400. In other embodiments, the threaded engagement between the collet 466 and the sleeve 468 can be omitted and the sleeve can simply be pressed down over the collet to compress the collet into engagement with the implant 400. The sleeve portion 468 can include any of the cooling means described herein, for example an internal chamber coupled to a cooling fluid system or a thermoelectric cooling system. In the illustrated embodiment, inlet and outlet conduits 422, 428 are provided to supply and evacuate cooling fluid to/from the sleeve portion 468. The instrument 402 defines a first heat exchange surface at the interface between the sleeve 468 and the collet 466, and a second heat exchange surface at the interface between the collet 466 and the implant 400. As cooling fluid is circulated through the sleeve 468, or some other coolant means is activated, the sleeve 468 is cooled. By extension, this cooling effect is applied to the collet 466, the implant 400, the bone in which the implant is implanted, and the target tissue disposed in proximity to the bone.

The illustrated instrument 402, and any of the other instruments disclosed below, can include one or more cut-outs (not shown) to facilitate placement of the instrument over a bone screw or receiver having a connecting rod already mounted therein. The instruments disclosed herein can also be sized and shaped to cover or mate to only an upper portion of a bone screw or receiver (e.g., a portion of the bone screw or receiver above a connecting rod mounted therein). The instruments disclosed herein can thus be coupled to a bone screw or receiver before or after a spinal connecting rod is mounted thereto.

Figure 5:
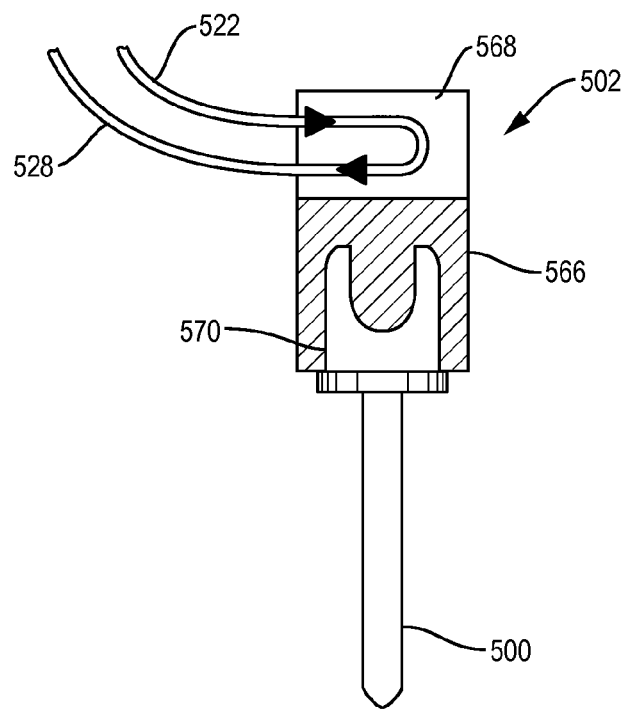
FIG. 5 is a cross-sectional view of another exemplary embodiment of a cooling instrument coupled to a bone screw.

FIG. 5 illustrates another exemplary embodiment of a cooling instrument or clamp 502. The instrument 502 includes an adapter 566 and a head portion 568 and is configured to be coupled to an implant 500 (e.g., a rod-receiving head of a bone screw or a rod-receiving member coupled to a bone screw) or to at least a portion of an anatomical structure such as a bone. The adapter 566 includes a distal recess 570 sized and shaped to receive a portion of the implant 500 therein (e.g., the rod-receiving portion of a bone screw or other connecting assembly). In some embodiments, the adapter recess 570 can be machined as a substantial negative of the corresponding portion of the implant 500, optionally with slightly smaller dimensions to produce an interference fit. The adapter 566 can be formed from a variety of materials, including conformable materials such as copper, silver, gold, nickel, tin, and various conformable alloys and thermally conductive polymers. In some embodiments, the adapter 566 can be in the form of a molded or formed polymeric boot, e.g., a boot formed from a highly conformable, low-modulus, filled-silicone polymer on a rubber-coated fiberglass carrier, such as Gap Pad® material available from The Bergquist Company. In some embodiments, such materials can have a thermal conductivity in the range of about 0.8 W/m-K to about 2.7 W/m-K.

In use, the instrument 502 can be engaged with the implant 500 via any of an interference fit, a snap fit, a press-fit, or the like. The head portion 568 can be formed integrally with the adapter 566 or can be coupled thereto using any of a variety of techniques. The head portion 568 can include any of the cooling means described herein, for example an internal chamber coupled to a cooling fluid system or a thermoelectric cooling system. In the illustrated embodiment, inlet and outlet conduits 522, 528 are provided to supply and evacuate cooling fluid to/from the head portion 568. The head portion 568 can be formed from any of a variety of thermally-conductive materials, including aluminum, titanium, stainless steel, thermally conductive polymers, or platinum. The instrument 502 defines a first heat exchange surface at the interface between the head 568 and the adapter 566, and a second heat exchange surface at the interface between the adapter 566 and the implant 500. As cooling fluid is circulated through the head portion 568, or some other coolant means is activated, the head portion is cooled. By extension, this cooling effect is applied to the adapter portion 566, the implant 500, the bone in which the implant is implanted, and the target tissue disposed in proximity to the bone.

Figure 6:
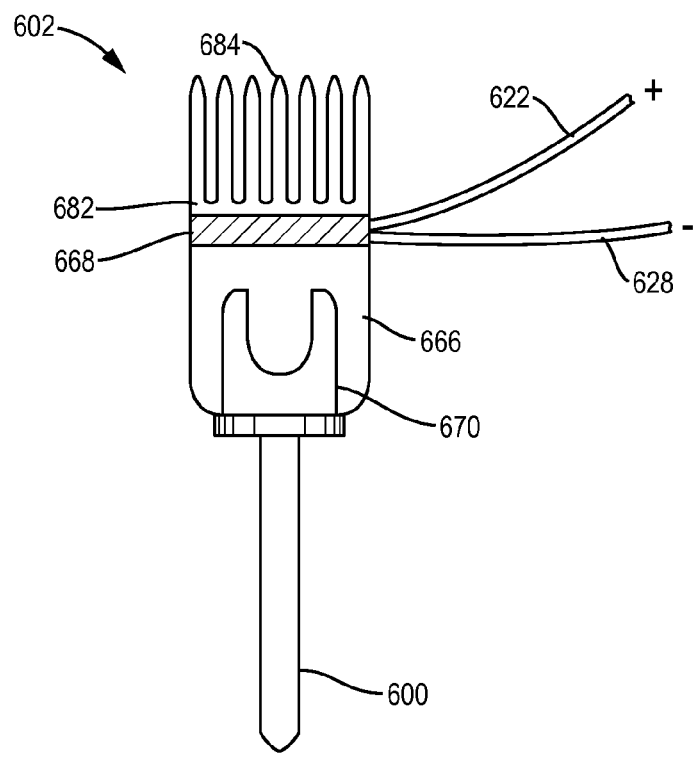
FIG. 6 is a cross-sectional view of another exemplary embodiment of a cooling instrument coupled to a bone screw.

FIG. 6 illustrates another exemplary embodiment of a cooling instrument or clamp 602. The instrument 602 includes an adapter 666, a thermoelectric module 668, and a heat sink 682, and is configured to be coupled to an implant 600 (e.g., a rod-receiving head of a bone screw or a rod-receiving member coupled to a bone screw) or to at least a portion of an anatomical structure such as a bone. The adapter 666 includes a distal recess 670 sized and shaped to receive a portion of the implant 600 therein (e.g., the rod-receiving portion of a bone screw or other connecting assembly). In some embodiments, the adapter recess 670 can be machined as a substantial negative of the corresponding portion of the implant 600, optionally with slightly smaller dimensions to produce an interference fit. The adapter 666 can be formed from a variety of materials, including conformable materials such as copper, silver, gold, nickel, tin, and various conformable alloys and thermally conductive polymers. In some embodiments, the adapter 666 can be in the form of a molded or formed polymeric boot, e.g., a boot formed from a highly conformable, low-modulus, filled-silicone polymer on a rubber-coated fiberglass carrier, such as Gap Pad® material available from The Bergquist Company. In some embodiments, such materials can have a thermal conductivity in the range of about 0.8 W/m-K to about 2.7 W/m-K.

In use, the instrument 602 can be engaged with the implant 600 via any of an interference fit, a snap fit, a press-fit, or the like. The thermoelectric module 668 can be formed integrally with the adapter 666 or can be coupled thereto using any of a variety of techniques. Any of a variety of thermoelectric cooling devices can be used for the thermoelectric module 668, including a Peltier device as described above. In the illustrated embodiment, first and second electrical leads or wires 622, 628 provide a current path between an external source and the thermoelectric module 668. It will be appreciated, however, that the thermoelectric module 668 can include an onboard power supply, e.g., a battery. The heat sink 682 is coupled to the thermoelectric module 668 and is configured to remove and dissipate heat generated by the thermoelectric module. The heat sink 682 can include a plurality of fins 684 to increase the heat dissipating surface area of the heat sink. The heat sink 682 can be formed from any of a variety of thermally-conductive materials, including aluminum, titanium, stainless steel, thermally conductive polymers, or platinum. The instrument 602 defines a first heat exchange surface at the interface between the thermoelectric module 668 and the adapter 666, and a second heat exchange surface at the interface between the adapter 666 and the implant 600. As the thermoelectric module 668 is activated, the adapter portion 666 coupled thereto is cooled. By extension, this cooling effect is applied to the implant 600, the bone in which the implant is implanted, and the target tissue disposed in proximity to the bone.

Figure 7A:
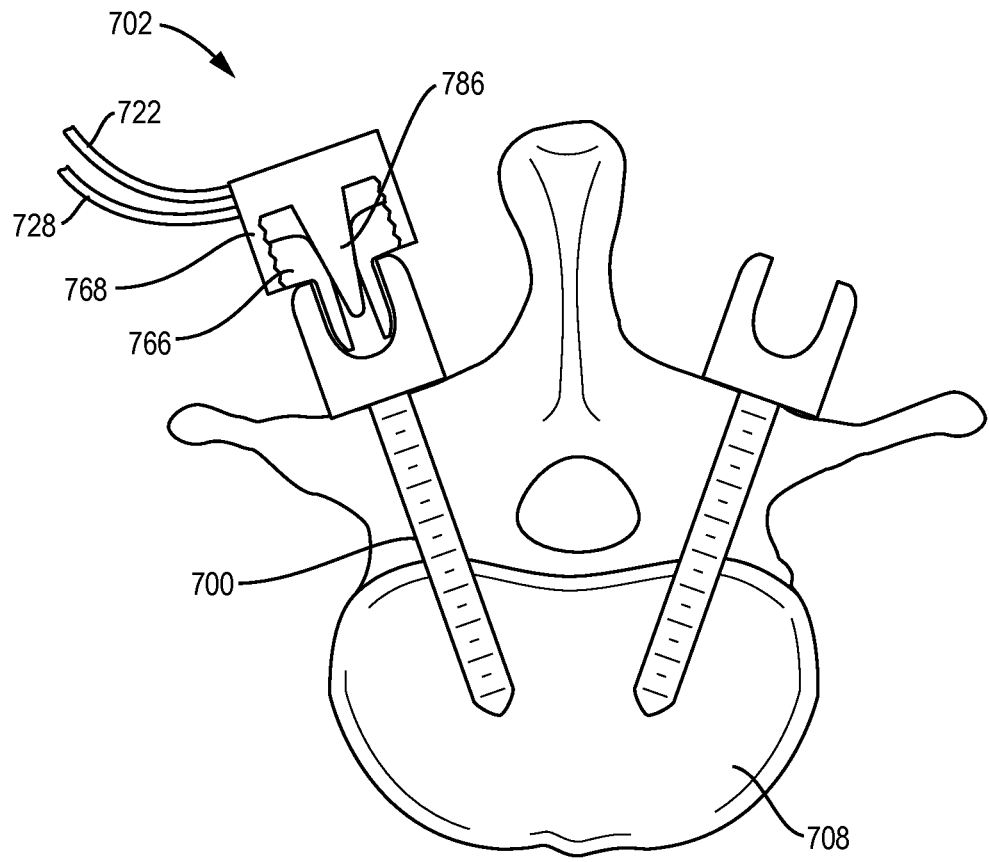
FIG. 7A is a cross-sectional view of another exemplary embodiment of a cooling instrument coupled to a bone screw implanted in a vertebra.
Figure 7B:
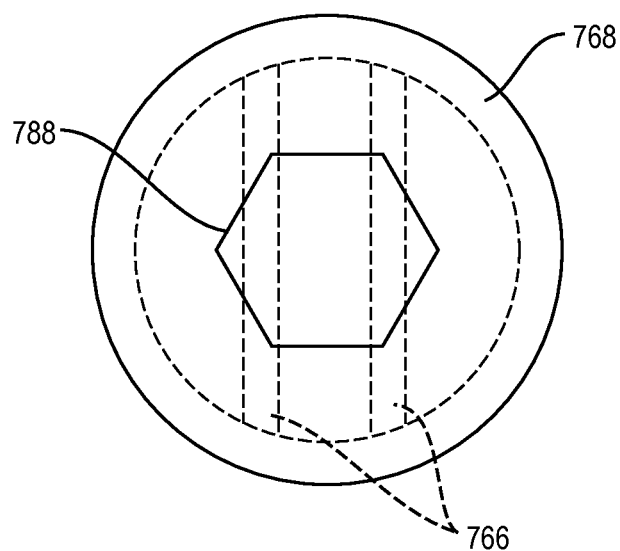
FIG. 7B is another cross-sectional view of the cooling instrument of FIG. 7A.
Figure 8A:
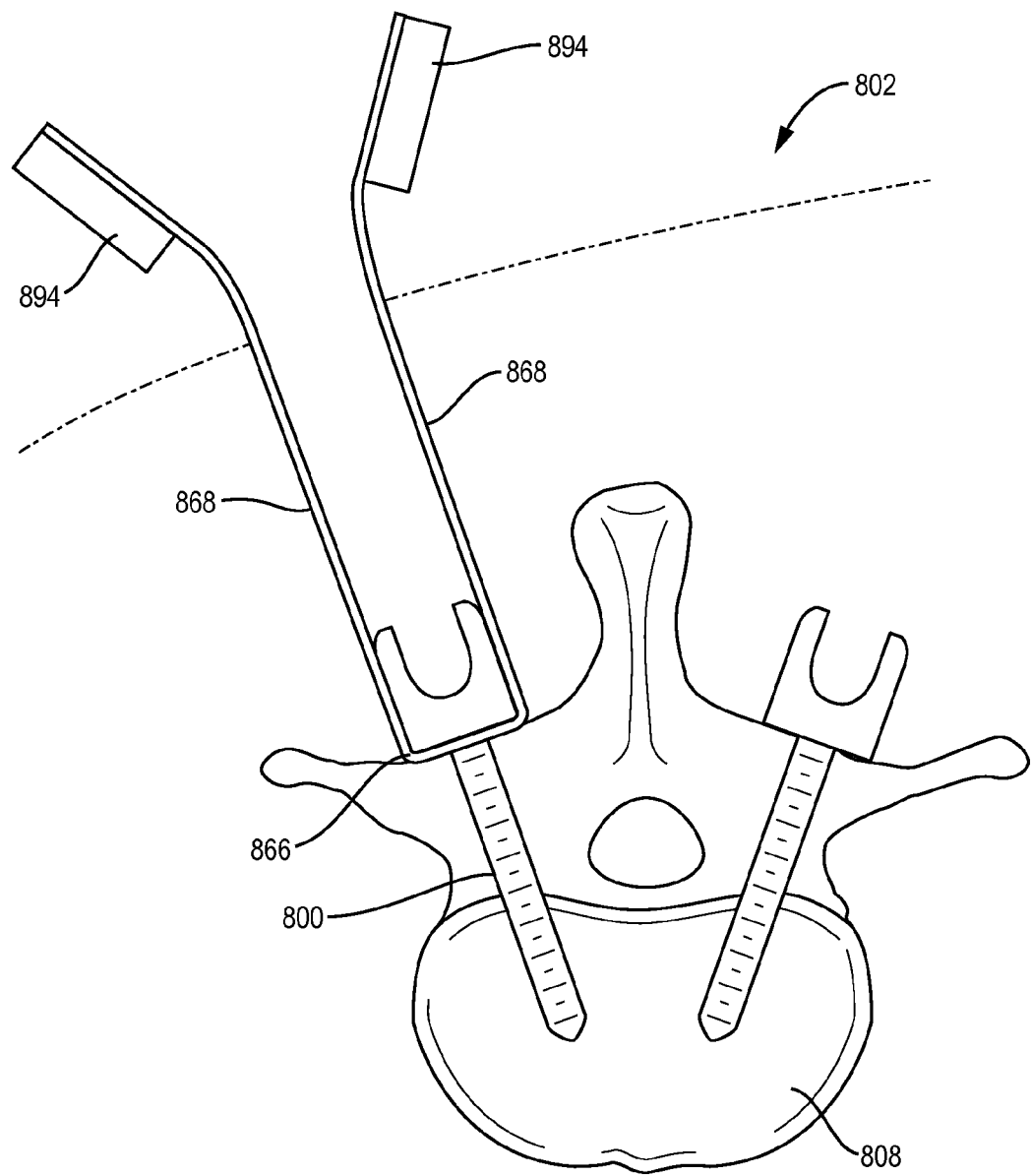
FIG. 8A is a cross-sectional view of another exemplary embodiment of a cooling instrument coupled to a bone screw implanted in a vertebra.
Figure 8B:
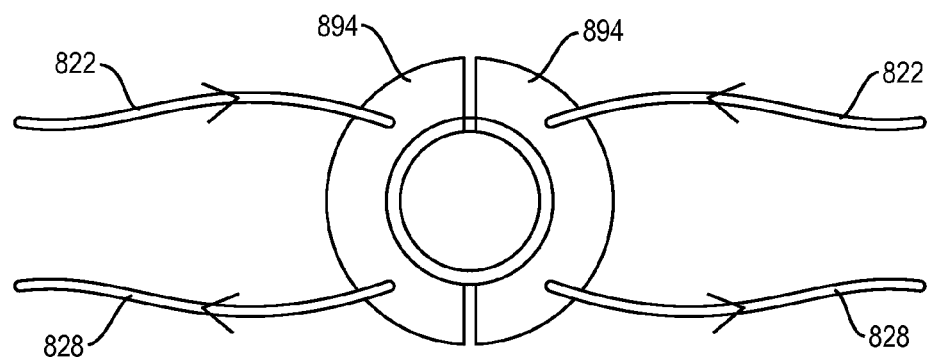
FIG. 8B is a top view of the cooling instrument of FIG. 8A.
Figure 8C:
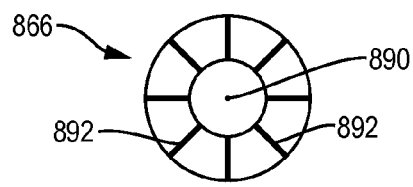
FIG. 8C is a bottom view of the cooling instrument of FIG. 8A.
Figure 8D:
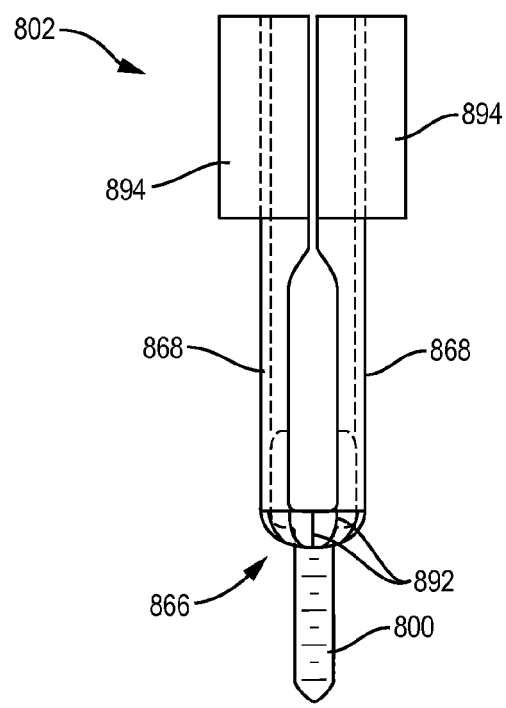
FIG. 8D is a side view of the cooling instrument of FIG. 8A.

FIGS. 7A-7B illustrate another exemplary embodiment of a cooling instrument or clamp 702. The instrument 702 includes an expandable collar 766 and a tightening nut 768, and is configured to be coupled to an implant 700 (e.g., a rod-receiving head of a bone screw or a rod-receiving member coupled to a bone screw) or to at least a portion of an anatomical structure such as a bone (e.g., a hole formed in a bone). In the illustrated embodiment, the collar 766 is sized and shaped to be received within a portion of the implant 700 (e.g., the rod-receiving portion of a bone screw or other connecting assembly). The collar 766 can include first and second halves which each include ramped surfaces and exterior threads. The tightening nut 768 can include interior threads configured to engage the exterior threads of the collar 766. The tightening nut 768 can also include a wedge portion 786 configured to engage the ramped surfaces of the collar 766 to expand the collar into firm engagement with a corresponding portion of the implant 700 (or a bone opening, as the case may be).

The tightening nut 768 and/or the collar 766 can include any of the cooling means described herein, for example an internal chamber coupled to a cooling fluid system or a thermoelectric cooling system. In the illustrated embodiment, inlet and outlet conduits 722, 728 are provided to supply and evacuate cooling fluid to/from the tightening nut 768. The tightening nut 768 and the collar 766 can be formed from any of a variety of thermally-conductive materials, including copper, silver, gold, nickel, tin, aluminum, titanium, stainless steel, thermally conductive polymers, platinum, and so forth. The tightening nut 768 can include a driving interface 788, as shown in FIG. 7B. The instrument 702 defines a first heat exchange surface at the interface between the tightening nut 768 and the collar 766, and a second heat exchange surface at the interface between the collar 766 and the implant 700.

In use, the collar 766 can be placed into a corresponding receiving portion of an implant or a bone opening. The tightening nut 768 can then be threaded onto the collar 766 and tightened, such that the wedge portion 786 drives the collar into firm engagement with the implant or surrounding bone. As cooling fluid is circulated through the tightening nut 768, or some other coolant means is activated, the tightening nut is cooled. By extension, this cooling effect is applied to the collar portion 766, the implant 700, the bone 708 in which the implant is implanted, and the target tissue disposed in proximity to the bone.

FIGS. 8A-8D illustrate another exemplary embodiment of a cooling instrument or clamp 802. The instrument 802 includes a washer portion 866 having first and second extension arms 868 projecting proximally therefrom, and is configured to be coupled to an implant 800 (e.g., a bone screw). The washer 866 includes a central opening 890 through which the shank of a bone screw 800 can be received. The proximal surface of the washer 866 can define a polyaxial seat in which the head of the bone screw 800 can be received, such that the instrument 802 can be positioned at a variety of angles relative to the bone screw. The washer 866 can be formed from a conformable material such that tightening of the bone screw 800 within the bone 808 compresses the washer and causes the washer to deform into intimate engagement with the head of the bone screw, thereby increasing the contact surface area therebetween. Exemplary conformable materials with high thermal conductivity include copper, silver, gold, nickel, tin, and various conformable alloys and thermally conductive polymers. The washer 866 can also include a plurality of radially extending grooves or shear lines 892 configured to shear apart when sufficient proximal pulling force is exerted on the instrument 802.

The extension arms 868 can define a rod-receiving channel therebetween and can be sized to extend from a distal portion positioned in contact with a bone screw 800 implanted in bone to a proximal portion positioned external to the patient. The extension arms 868 and the washer 866 can be formed integrally or can be coupled to one another. The extension arms 868 and/or the washer 866 can include any of the cooling means described herein, for example an internal chamber coupled to a cooling fluid system or a thermoelectric cooling system. In the illustrated embodiment, shown for example in FIG. 8B, each of the extension arms 868 includes its own cooling means 894 disposed external to the patient and supplied by respective inlet and outlet conduits 822, 828. The extension arms 868 can be coated with an insulating material (e.g., sprayed-on silicone) such that thermal energy transfer between the extension arms and surrounding tissue is minimized, thereby protecting the surrounding tissue and increasing the efficiency with which the washer 866 can be cooled by thermal energy conducted through the inner core of the extension arms 868. The extension arms 868 can be formed from the same material as the washer 866 or can be formed from a different material. The instrument 802 defines a heat exchange surface at the interface between the washer 866 and the implant 800.

In use, a bone screw or other implant 800 is inserted through the central opening 890 in the washer 866, positioned in proximity to a bone 808, and advanced into the bone. As the implant 800 is tightened, the washer 866 is compressed and substantially conforms to the shape of the implant, maximizing the contact area therebetween. As cooling fluid is circulated through the coolant means 894 of the extension arms 868, the arms are cooled. By extension, this cooling effect is applied to the washer 866, the implant 800, the bone 808 in which the implant is implanted, and the target tissue disposed in proximity to the bone. When the cooling regimen is completed, the extension arms 868 can be pulled proximally, optionally with the use of a specialized tool, to cause the washer 866 to shear apart along the shear lines 892 and thereby separate the cooling instrument 802 from the implant 800.

The embodiment of FIGS. 8A-8D can provide a number of advantages. For example, the coolant means can be disposed external to the patient, allowing the implantable portion to remain small and the heat exchange surface between the coolant means the extension arms to be made large. In addition, the length of the extension arms and the ability to remove the instrument by shearing the washer allow the instrument to be installed and removed using a percutaneous or minimally-invasive approach. The conformable nature and/or shape of the washer also allows the instrument to be used with screws or other implants having any of a variety of shapes, contours, etc., and increases the thermal connection between the instrument and the implant. Also, because the instrument is disposed outside of the rod-receiving recess of the implant, rod placement and manipulation can be performed while actively cooling and/or before removing the cooling instrument from the patient.

Figure 9:
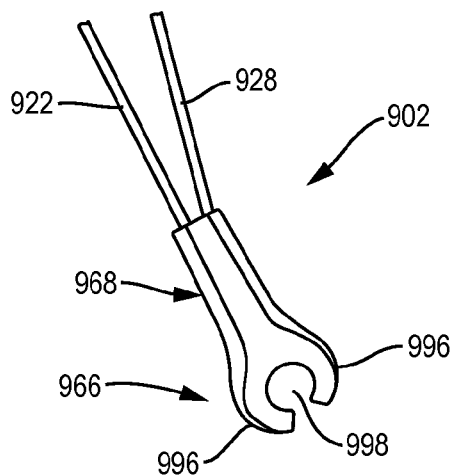
FIG. 9 is a perspective view of another exemplary embodiment of a cooling instrument.

FIG. 9 illustrates another exemplary embodiment of a cooling instrument or clamp 902. The instrument 902 includes a body portion 968 and a claw portion 966, and is configured to be coupled to an implant (e.g., a spinal connecting rod or the neck of a bone screw) or to an anatomical structure such as a bone. The claw portion 966 can be substantially C-shaped and can include first and second arms 996. The arms 996 can be flexible and resilient, such that the arms can be deflected slightly to capture a portion of an implant or a bone within the grasp of the claw 966 and can then spring back towards their initial position. The arms 996 can define an opening 998 that extends more than 180 degrees around a circular implant or bone portion, such that the implant or bone portion can be captured and retained within the opening 998. In exemplary embodiments, the arms 996 can extend between about 200 degrees and about 300 degrees around the circular opening 998. It will be appreciated that the opening 998 can have shapes other than circular, and that the shape of the opening can be selected based on a variety of factors, such as the shape of the implant or bone to which the instrument 902 is to be coupled.

The claw portion 996 and the body portion 968 can be formed from a variety of materials, including conformable materials such as copper, silver, gold, nickel, tin, and various conformable alloys and thermally conductive polymers. The body portion 968 and the claw portion 966 can be formed integrally or can be coupled to one another. The body portion 968 and/or the claw portion 966 can include any of the cooling means described herein, for example an internal chamber coupled to a cooling fluid system or a thermoelectric cooling system. In the illustrated embodiment, the body portion 968 includes a cooling means coupled to inlet and outlet conduits 922, 928. The instrument 902 defines a heat exchange surface at the interface between the claw portion 966 and the implant or bone to which the instrument 902 is coupled.

In use, the arms 996 of the claw portion 966 are deformed slightly to allow a portion of an implant or a bone to be positioned within the opening 998 defined by the arms. The resilient properties of the arms 996 allow them to spring back towards their initial position, thus permitting the claw 966 to snap or clip onto the implant or bone and thereby capture or retain the implant or bone therein. As cooling fluid is circulated through the body portion 968, or some other coolant means is activated, the body portion and the claw portion 966 are cooled. By extension, this cooling effect is applied to the implant, the bone in which the implant is implanted, and the target tissue disposed in proximity to the bone.

Figure 10A:
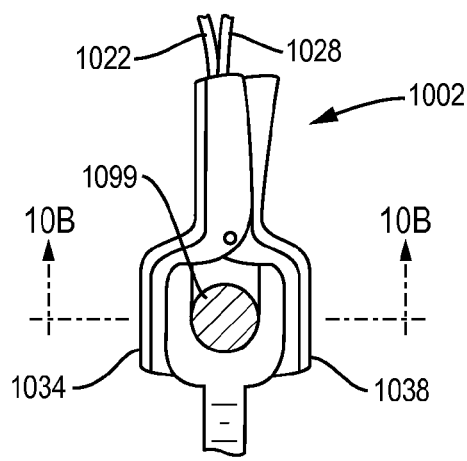
FIG. 10A is a side view of another exemplary embodiment of a cooling instrument coupled to a bone screw.
Figure 10B:
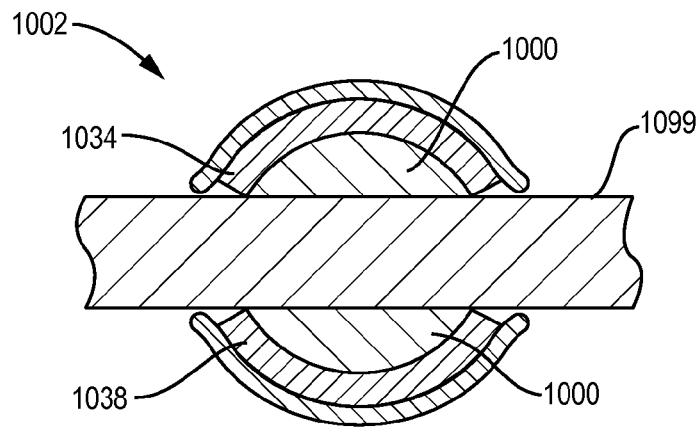
FIG. 10B is a cross-sectional view of the cooling instrument of FIG. 10A.

FIGS. 10A-10B illustrate another exemplary embodiment of a cooling instrument or clamp 1002. Except as indicated, the structure and function of the instrument 1002 is substantially the same as that of the instrument 102 described above, and therefore a detailed description thereof is omitted here for the sake of brevity. As shown in FIG. 10B, the implant-contacting, heat exchange surfaces of the jaws 1034, 1038 can be shaped to correspond to the exterior dimensions of an implant 1000 (e.g., the head portion of a bone screw or a member coupled to a bone screw that is configured to receive a connecting rod 1099). In particular, the implant-contacting surface can be substantially a negative of a corresponding surface of the implant 1000.

FIG. 11 illustrates another exemplary embodiment of a cooling instrument 1102. The instrument 1102 includes a bone screw 1100 and one or more detachable towers 1168 configured to be selectively coupled to the bone screw. While a bone screw is shown in the illustrated embodiment, it will be appreciated that any of a variety of implants can be used in the cooling instrument 1102. The towers 1168 can be of the type typically used (without cooling features) in percutaneous pedicle screw placement, or of the type typically used (without cooling features) as removable rod-receiver extension tabs for spondylolisthesis reduction.

Figure 11A:
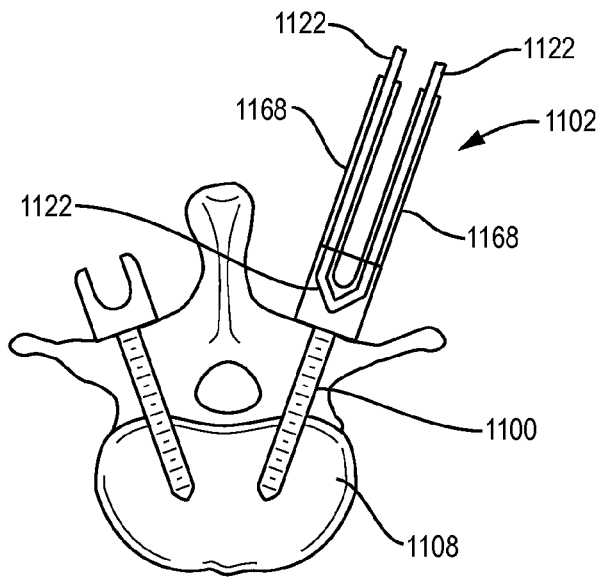
FIG. 11A is a cross-sectional view of another exemplary embodiment of a cooling instrument.
Figure 11B:
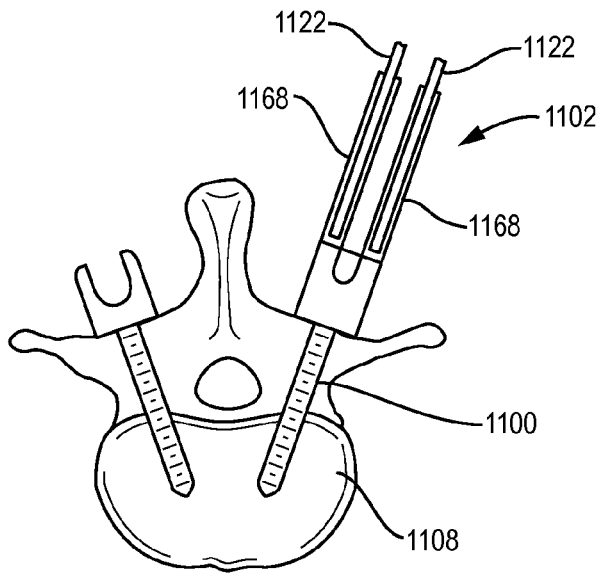
FIG. 11B is a cross-sectional top view of another exemplary embodiment of a cooling instrument coupled to a bone screw.
Figure 11C:
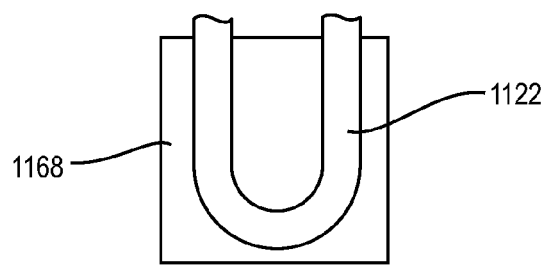
FIG. 11C is a cross-sectional side view of the cooling instrument of FIG. 11B.

The detachable towers 1168 can define a rod-receiving channel therebetween and can be sized to extend from a distal portion positioned in contact with the bone screw 1100 implanted in bone to a proximal portion positioned external to the patient. The towers 1168 can be coupled to various parts of the bone screw or implant (e.g., a head portion of the bone screw having a U-shaped rod-receiving channel formed therein) using various techniques (e.g., a threaded interface, a snap-fit, an interference-fit, a frangible or break-away portion, and so forth). The towers 1168 and/or the bone screw 1100 can include any of the cooling means described herein, for example an internal chamber coupled to a cooling fluid system or a thermoelectric cooling system. In the embodiment of FIG. 11A, a cooling means (not shown) is disposed external to the patient and circulates cooling fluid through a conduit 1122 that extends through the towers 1168 and at least a portion of the bone screw 1100. In other embodiments, e.g., as shown in FIGS. 11B-11C, each tower can include its own independent conduit 1122, and the conduits 1122 can extend only through the towers 1168 (i.e., not through the bone screw 1100). At least a portion of the towers 1168 can be coated with an insulating material (e.g., sprayed-on silicone) such that thermal energy transfer between the towers and surrounding tissue is minimized, thereby protecting the surrounding tissue and increasing the efficiency with which the bone screw 1100 can be cooled by thermal energy conducted through the conduit 1122. The instrument 1102 defines a heat exchange surface at least at the interface between the bone screw 1100 and the surrounding tissue.

In use, the bone screw 1100 is inserted through a tissue opening, positioned in proximity to a bone 1108, and advanced into the bone. Cooling fluid can then be circulated through the conduit 1122 of the towers 1168 and/or the bone screw 1100 to cool the bone 1108 in which the bone screw is implanted and the target tissue disposed in proximity to the bone. When the cooling regimen is completed, the towers 1168 can be detached from the bone screw 1100 (e.g., by breaking a frangible portion or decoupling a threaded or snap-fit interface).

The embodiments of FIGS. 11A-11C can provide a number of advantages. For example, the coolant means can be disposed external to the patient, allowing the implantable portion to remain small and the heat exchange surface between the coolant means the towers 1168 to be made large. In addition, the length of the towers and the ability to detach the towers from the implant allow the instrument to be installed and removed using a percutaneous or minimally-invasive approach. Also, because the cooling aspects of the instrument are disposed outside of the rod-receiving recess of the implant, rod placement and manipulation can be performed while actively cooling and/or before removing the cooling instrument from the patient.

It will be appreciated that the instruments and hardware described herein are able to be produced using common practices known to those skilled in the art of hardware manufacturing and specifically surgical device manufacturing.

The cooling instruments, implants, and related hardware disclosed herein can be formed from any of a variety of thermally-conductive, medical-grade, and/or implantable materials such as metals, plastics, ceramics, and the like. Metals typically have high thermal conductivity which is advantageous for the implementation of the cooling instrument, as it provides for rapid conduction of the cooling effect. Secondly, metal typically has high physical strengths (e.g. tensile, shear, compressive) which is advantageous as it reduces risks of fracture or deformation. Metal also is able to be readily sterilized, which can be a critical attribute for use with live patients. In some embodiments, the cooling instrument can be formed from biocompatible titanium or stainless steel.

The size (e.g., length, width, diameter, etc.) of the cooling instrument and in particular of the heat exchange surfaces thereof can be selected based on a variety of factors, including the dimensions of the bone structure or implant to which the cooling effect is to be applied, the age, sex, or species of the patient, and/or the degree of cooling required.

Methods

Figure 12A:
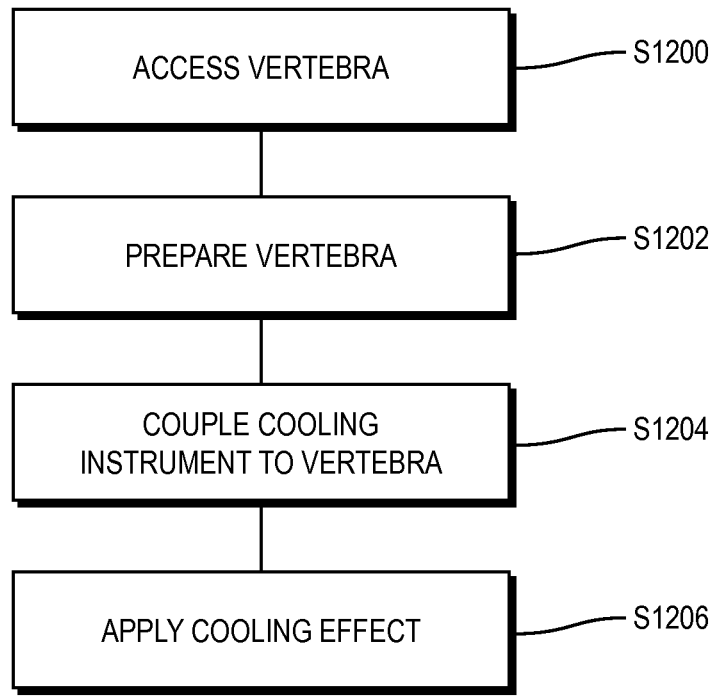
FIG. 12A is a flow chart of an exemplary method for cooling tissue.
Figure 12B:
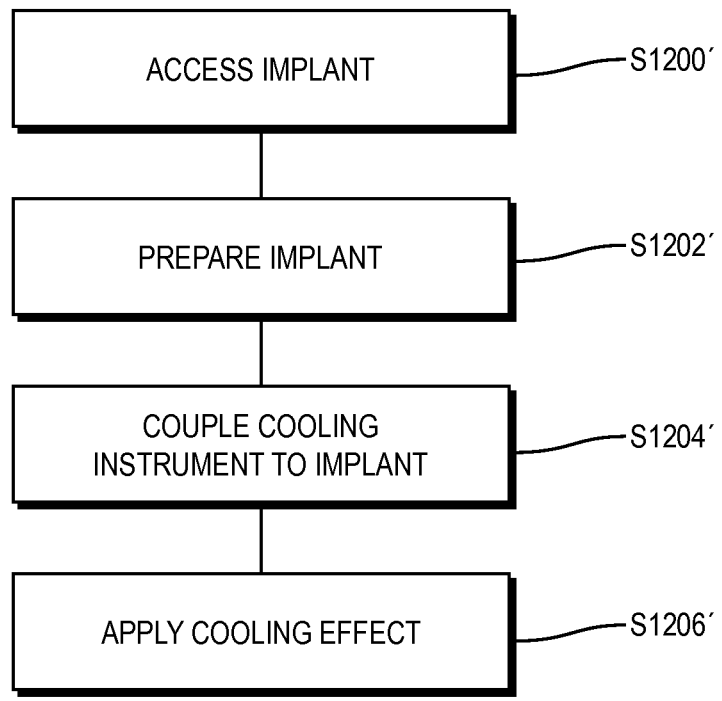
FIG. 12B is a flow chart of another exemplary method for cooling tissue.

FIGS. 12A and 12B are flow charts of exemplary methods of cooling tissue. While various methods disclosed herein are shown in relation to a flow chart or flow charts, it should be noted that any ordering of method steps implied by such flow charts or the description thereof is not to be construed as limiting the method to performing the steps in that order. Rather, the various steps of each of the methods disclosed herein can be performed in any of a variety of sequences. In addition, as the illustrated flow charts are merely exemplary embodiments, various other methods that include additional steps or include fewer steps than illustrated are also within the scope of the present invention. Furthermore, two or more of the illustrated steps can be performed simultaneously.

FIG. 12A illustrates a method of cooling spinal tissue by clamping a cooling instrument directly to a bony structure of a vertebra. In step S1200, access to a vertebra is obtained, for example using an open or minimally-invasive surgical technique to form a tissue opening through which the vertebra can be accessed. In step S1202, the bony structure of the vertebra can be prepared to receive the cooling instrument. Such preparation can include resecting soft tissue to expose the underlying bone, irrigating, scraping, or rasping the bone, and/or any of a variety of other surgical procedures familiar to those skilled in the art of spinal surgery. As noted above, the bony structure of the vertebra can be any part of the vertebra, including without limitation a pedicle, lamina, posterior arch, transverse process, spinous process, articular process, vertebral body, etc.

Once the bone is prepared, the cooling instrument can be advanced through the tissue opening and coupled to the bone in step S1204. A cooling effect can then be delivered to the bone, via the cooling instrument, in step S1206. This can be accomplished, for example, by expanding gas through the cooling instrument causing it to rapidly cool itself and the tissues adjacent to it. Alternatively, other coolant means can be used besides gas expansion, including circulating chilled fluid through the cooling instrument, as well as powering a Peltier device in the cooling instrument. The delivery of the cooling effect, in some implementations, includes delivering the coolant means from a coolant source, such as a tank of compressed gas. In this step, the tank of compressed gas can be opened such that the compressed gas flows through a tube (e.g., a coolant delivery conduit) to the cooling instrument. The tank can include a regulation or control unit that controls how much and how fast compressed gas is delivered to the cooling instrument. The control unit can simply be a manually operated valve, in which case the delivering of the cooling effect is initiated by manually opening the valve. The control unit can also include a computer-controlled valve that uses either pre-programmed data or perioperatively-measured data to determine how much of a cooling effect should be delivered.

For instance, the control unit can read data from a temperature sensor placed intrathecally, and when the intrathecal temperature is reduced below a threshold value, the control unit can begin to limit or turn off the delivery of the cooling effect. When the intrathecal temperature rises above the temperature threshold, the control unit can begin delivering the cooling effect again. It will be appreciated that any number of physiological characteristics (as previously mentioned), both quantitative and qualitative, can be used as input to the control unit for the purposes of controlling the delivery of the cooling effect.

The cooling instrument can remain implanted in the patient for only the duration of the delivery of the cooling effect, or can remain implanted in the patient after the surgical wound has been closed up (e.g., after disconnecting the inlet and outlet conduits from the cooling instrument).

It will be appreciated that the steps described above can be repeated for a plurality of cooling instruments, each of which can be positioned in different positions within a patient's vertebrae. In one exemplary embodiment, a first cooling instrument is clamped onto a first vertebra and a second cooling instrument is clamped onto a second vertebra. In another exemplary embodiment, a first cooling instrument is clamped onto a first transverse process of a first vertebra and a second cooling instrument is clamped onto a second, contralateral transverse process of the first vertebra. Cooling instruments can thus be coupled to multiple vertebral levels of the patient's spine, and any number of cooling instruments can be couple to a single vertebra. In one embodiment, a location of spinal injury is determined and cooling instruments are coupled to one, two, or three vertebrae superior to the location of spinal injury. In another embodiment, cooling instruments are coupled to the vertebrae that are immediately superior and inferior to the site of the spinal injury.

The method of FIG. 12A can also include installation of stabilization hardware to stabilize the patient's spine. For example, bone screws, hooks, rods, plates, and the like can be coupled to the patient's spine.

FIG. 12B illustrates a method of cooling spinal tissue by clamping a cooling instrument to an implant which is implanted in a bony structure of a vertebra or coupled to an implant that is implanted in a bony structure of a vertebra. In step S1200', access to the implant is obtained, for example using an open or minimally-invasive surgical technique to access a previously-implanted implant, or by performing any of a variety of known surgical procedures to install an implant in the patient (e.g., a spinal stabilization or fusion procedure). In step S1202', the implant can be prepared to receive the cooling instrument. Such preparation can include removing any debris from the implant or otherwise cleaning or polishing the implant, particularly the surface of the implant to be used as a heat exchange surface.

Once the implant is prepared, the cooling instrument can be advanced through the tissue opening and coupled to the implant in step S1204'. A cooling effect can then be delivered through the cooling instrument to the implant, and by extension to bone and other tissue disposed in proximity to the implant, in step S1206'. This can be accomplished, for example, by expanding gas through the cooling instrument causing it to rapidly cool itself and the tissues adjacent to it. Alternatively, other coolant means can be used besides gas expansion, including circulating chilled fluid through the cooling instrument, as well as powering a Peltier device in the cooling instrument.

It will be appreciated that the steps described above can be repeated for a plurality of cooling instruments, each of which can be positioned in different positions within a patient's vertebrae. In one exemplary embodiment, a first cooling instrument is clamped onto a first implant and a second cooling instrument is clamped onto a second implant.

Hypothermia Delivery—Temperature & Time

The methods and devices described herein generally involve applying localized therapeutic hypothermia and, in some cases, cooling the tissue in and around the spinal cord. Various hypothermic instrumentations are described to deliver a cooling effect to the spinal canal, and to the spinal cord itself. "Therapeutic hypothermia" as used herein refers to the reduction of tissue temperature below a patient's normal body temperature, typically about 37 degrees C. Therapeutic hypothermia can also include reduction of tissue temperature below a patient's body temperature when treatment is initiated, which may not be the patient's normal body temperature (e.g., when the patient presents with a fever or in an already-hypothermic state, for example due to previous or ongoing systemic hypothermia treatment).

The degree of hypothermia applied can vary upon a number of factors. Target therapeutic temperatures can range from just below 0 degrees C. to just below normothermia. Tissue exposure to temperatures below 0 degrees C. can lead to cellular damage, however the bones of the spinal column are relatively resilient to such low temperatures and therefore target therapeutic temperatures can be below 0 degrees C. in some embodiments.

In an exemplary embodiment, the target tissue is cooled to within a range of about 0 degrees C. to about 37 degrees C. The target tissue can also be cooled to within a range of about 5 degrees C. to about 36 degrees C., more preferably about 15 degrees C. to about 36 degrees C., more preferably about 25 degrees C. to about 36 degrees C., more preferably about 25 degrees C. to about 35 degrees C., and more preferably about 30 degrees C. to about 34 degrees C. In certain embodiments, the target tissue can be cooled to about 36 degrees C., about 35 degrees C., about 34 degrees C., about 33 degrees C., about 32 degrees C., about 31 degrees C., or about 30 degrees C. In other aspects, the target tissue can be cooled to about 1 degree C. below normothermia, about 2 degrees C. below normothermia, about 5 degrees C. below normothermia, about 10 degrees C. below normothermia, or about 20 degrees C. below normothermia.

Degrees of hypothermia are sometimes described in terms of "mild" hypothermia (e.g., 0-5 degrees C. below normothermia), "moderate" hypothermia (e.g., 5-9 degrees C. below normothermia), "severe" hypothermia (e.g., 9-17 degrees C. below normothermia), and "profound" hypothermia (e.g., more than 17 degrees C. below normothermia). The methods disclosed herein can include cooling of tissue to within any of these ranges, and the systems and devices disclosed herein can be configured to achieve such cooling. Various treatment protocols can also be used in which the tissue temperature is cycled, pulsed, swept, ramped, and/or stepped through these or other ranges. For example, in one treatment method, the tissue temperature can be quickly lowered to a target temperature and then slowly ramped back up to normothermia when it is desired to cease treatment. By way of further example, the tissue temperature can be slowly stepped down to a first target temperature, oscillated between the first target temperature and a second target temperature, and then eventually stepped back up to normothermia.

The duration of exposure of the target tissue to the cooling effect can range from minutes to days depending on a variety of factors, including the patient's condition, the treatment of the patient's other injuries, the prospective treatment protocol for the patient, and monitored or detectable physiological responses, or lack thereof, to the cooling. Therapeutic hypothermia can be applied in a single procedure or multiple times. In either case, a multiplicity of different temperatures can be applied. Preferably, when discussing target temperatures, it is intended to mean the desired therapeutic temperature of the targeted tissue. Alternatively, target temperature at times can also refer to the temperature of the cooling instrument or the cooling chamber or element of the cooling instrument. It will be appreciated that it can be necessary in some instances to cool the cooling instrument to below the target tissue temperature in order for the target tissue to reach the target tissue temperature.

The methods described herein can include cooling the spinal canal tissue and the spinal cord for variable lengths of time and/or at different temperatures. In addition, cooling can occur in multiple doses, where each dose can differ from the others in exposure time and/or temperature. The determination of the exposure time(s) and temperature(s) can be predetermined based on known effective times and temperatures or can be determined based on the condition of the patient and/or when the treatment is applied relative to when the injury occurred. A wide variety of physiological effects, both local and systemic, can arise from the cooling of the target tissue (e.g., spinal canal tissue and the spinal cord) below normal body temperature. Exposure time, doses, and target temperature can be varied during the procedure based on monitored physiological parameters or characteristics as well as parameters of the cooling devices or systems.

These parameters include, but are not limited to, neurological findings, blood pressure, target-tissue temperature, specific tissue temperature (proximate to target tissue), core (rectal) body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, markers of excitotoxicity, vasogenic edema, apoptosis, inflammation, and enzymatic responses. The target temperature, doses, and exposure time can be selected by initial measurements of these physiological parameters and then modified based upon real-time measurement of these parameters. Effectively, the cooling regimen, in terms of temperatures, exposure times, and doses, can be controlled by measured physiological characteristics of the patient and the cooling devices and systems.

For example, a cooling effect can be applied initially at a predetermined target temperature based on the type and severity of injury incurred, including for example the vertebral level of injury. The cooling effect can be increased, and as such, the target temperature can be reduced, if after a predetermined period of time, the motor-evoked potential responses of the patient appear unremarkable. In one embodiment, if the difference between the arterial blood pressure and the cerebral spinal fluid pressure reduces below a predetermined threshold, the application of the therapeutic hypothermia can be stopped. It should be understood that there are any number of protocols that can be followed in the application of therapeutic hypothermia based on clinical, laboratory, and monitoring markers.

In one embodiment, therapeutic hypothermia is initiated as soon as possible following a spinal injury, e.g., less than 8 hours after the injury. Therapeutic hypothermia can be maintained up to 72 hours, up to 120 hours, or more. It can be desirable to deliver therapeutic hypothermia for a much shorter duration as well, including as little as a fraction of an hour (e.g., 5 minutes, 15 minutes, 30 minutes, or 45 minutes).

The use of therapeutic hypothermia on the spinal cord and the spinal canal can yield a variety of beneficial effects. Such effects can include the reduction of nervous tissue metabolic demand, excitotoxic markers, apoptosis, free-radicals, and inflammation. It should be noted that some of the mechanisms of action associated with therapeutic hypothermia are not fully understood, but experience with its application in a variety of clinical situations suggests a mitigating effect in spinal cord damage from trauma, vascular insult, or surgical insult.

Transosseous Cooling

In some of the methods and devices described herein, a cooling effect is applied transosseously, or through bone. In particular, tissue can be cooled by clamping a cooling instrument to adjacent or nearby bone or to an implant implanted in adjacent or nearby bone. Bone has properties that make it an advantageous cooling platform. Boney structures are readily locatable due to their greater density and rigidity than so-called soft tissues. Furthermore, their geometries are readily mapped radiographically, are relatively consistent between patients, and have easily locatable features or landmarks. Accordingly, particular surrounding or soft tissues are relatively consistently located in a known proximity to these bone structures and landmarks. In particular, vertebral pedicles and lamina lie in close proximity to the contents of the spinal canal, including the spinal cord and nerve roots.

These attributes allow specific surrounding soft tissue to be reliably targeted by using adjacently located bone structures and landmarks of the bone structures as a platform and avenue to put instruments near the specific soft tissue. Using bony structures and their landmarks as a means for targeting nearby or adjacent tissues helps avoid a need to directly target the tissue wishing to be treated, leaving the tissue undisturbed.

An advantageous aspect of a transosseous approach for providing a cooling effect to nearby soft tissue is the fact that bone is rigid, allowing for an instrument to be securely anchored into or on the bone, clamped to the bone, or clamped to an implant implanted in or near the bone, where the bone is not subject to deformation because of bodily movement or because of the instrument's presence. The rigid nature of the bone also allows a cooling instrument to be clamped thereto, or to an implant implanted therein, without disturbing the tissues outside of the bone.

A transosseous approach for providing a cooling effect to nearby soft tissue allows for the implantation or clamping of cooling instrumentation without disturbing the soft tissue itself. That is, by using a bone approach and cooling across the bone wall to the nearby tissue, the targeted nearby tissue is not physically touched, displaced, or incised by the cooling instrument or clamp or by the surgical steps needed to implant or clamp the cooling instrument. Certain tissues, such as spinal cord tissue, are delicate and sensitive to disturbances, and such disturbances could cause permanent injury to the tissues. As such, it can be undesirable to implant or clamp cooling instruments in these tissues or in nearby soft tissues due to risks of causing injury to the tissues. Bone is very resilient to such disturbances, and typically does not realize a great loss in function or strength and is typically not susceptible to long term injury from such disturbances. It is therefore desirable to clamp, attach, insert, or implant a cooling instrument into or on a bony structure and cool nearby soft tissue transosseously, or across the bone wall, thus allowing for reliable cooling access to soft tissue without physically disturbing the soft tissue itself.

In exemplary embodiments, the soft tissue that is targeted to be cooled is the spinal cord, other spinal canal tissue, and/or nerve root tissue, and the bony structures which act as the cooling platform are parts of a vertebra, including the elements of the posterior arch such as the pedicles, the lamina, and the spinous process. A transosseous approach for providing cooling across pedicle and/or lamina bone to the adjacent spinal canal contents targets the spinal cord without its actual contact, displacement, or penetration. This can be a critical consideration since the spinal cord's tolerance for such intrusions is likely minimal.

Concluding Statements

It will be understood that any of the methods and devices disclosed herein can be used on multiple vertebrae at once and/or multiple bony structures of each vertebra at once, by utilizing multiple cooling instruments at the same time. It will be understood that the methods and devices disclosed herein can be used for conditions other than traumatic spinal cord injury, including for cooling other tissues. The methods and devices can be used for other types of spinal cord injury, as well as for treating nerve root damage. The methods and devices can be used prophylactically. The methods and devices can be used before, during, and/or after an injury occurs and can be used pre-operatively, peri-operatively, and/or post-operatively with regard to any particular procedure that can be conducted.

Furthermore, the methods and devices can be used for non-injury related purposes. In particular, the methods and devices described herein can be used as an adjunctive procedure to an aneurysm repair surgery, such as thoracoabdominal aortic aneurysm repair or abdominal aortic aneurysm repair. In these procedures, it is common for blood flow to the spinal cord to be compromised, thus introducing a risk of ischemic spinal cord injury. The methods and devices described herein can provide a protective therapy during such ischemic periods.

Further, the methods and devices described herein can also be used for spinal fusion procedures where cooling is not initially intended. The methods and devices described herein can be used for fusion with the understanding that an intraoperative complication can occur (example: iatrogenic injury caused during scoliosis correction surgery) where having the capability to deliver a cooling effect can be desired.

The methods and devices described herein can be used prophylactically to deliver a cooling effect to nerve roots. Though such delivery of a cooling effect can be achieved with one cooling instrument, it can be better achieved by having two or more cooling instruments placed above and below the particular root that is being targeted. The delivery of a cooling effect to a nerve root can also occur peri-operatively or postoperatively.

It will be appreciated that the methods and devices disclosed herein can be used in other parts of a mammalian body, and in particular, can be used with orthopedic procedures to deliver a cooling effect to surrounding tissues.

The described aspects above are given as illustrative examples of those that fall within the scope of the subject matter described, but are not intended to limit that scope. The described devices and methods can be the sole devices and methods used and performed in the spine at the time of the herein described therapy or can accompany other devices and procedures such as those related to spinal decompression, reduction, stabilization, and fusion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Further details on methods and devices for cooling tissue, including methods and devices which can be used in conjunction with those described herein, are discussed in U.S. Publication No. 2011/0282418, published on Nov. 17, 2011, titled "METHODS AND DEVICES FOR COOLING SPINAL TISSUE," which is hereby incorporated by reference in its entirety.

The foregoing description has been presented for purposes of illustration and description. Many modifications and variations of the subject matter described will be apparent to those skilled in the art. Although the invention has been described by reference to specific embodiments, it should be understood that numerous changes can be made within the spirit and scope of the inventive concepts described. Accordingly, it is intended that the invention not be limited to the described embodiments, but that it have the full scope defined by the language of the following claims.

What is claimed is:

1. A tissue cooling system, comprising:
   an implant selected from the group consisting of a bone screw, a connecting rod, a plate, and a disk replacement implant;
   a clamp configured to grasp the implant, the clamp having a heat exchange surface; and
   a cooling mechanism in thermal communication with the clamp such that a cooling effect can be applied through the heat exchange surface to the implant when the implant is grasped by the clamp;
   wherein the heat exchange surface is shaped to correspond to the exterior dimensions of the implant such that the heat exchange surface is substantially a negative of a corresponding surface of the implant.

2. The device of claim 1, wherein the clamp includes a thermally-insulating surface.

3. The device of claim 1, wherein the cooling mechanism comprises a thermoelectric cooler.

4. The device of claim 1, wherein the cooling mechanism comprises:
   a cooling fluid delivery conduit;
   a cooling fluid exhaust conduit; and
   a cooling fluid chamber in fluid communication with the delivery conduit and the exhaust conduit and in thermal communication with the heat exchange surface of the clamp.

5. The device of claim 1, wherein the clamp comprises first and second movable jaws.

6. The device of claim 5, wherein the implant is a bone screw and the jaws are configured to substantially surround the head of the bone screw.

7. The device of claim 5, wherein the heat exchange surface comprises toothed gripping surfaces of the first and second movable jaws.

8. The device of claim 5, wherein the cooling mechanism is at least partially disposed within the first jaw.

9. The device of claim 5, further comprising a biasing element configured to bias the jaws toward a closed position.

10. The device of claim 5, further comprising a locking mechanism configured to lock the jaws in a particular position relative to one another.

11. The device of claim 5, further comprising a tightening screw configured to advance the jaws towards one another.

12. The device of claim 1, wherein the clamp is formed from a conformable material.

13. The device of claim 1, wherein the clamp comprises a thermally-conductive, polymeric boot portion and a metallic head portion in which the cooling mechanism is disposed.

14. The device of claim 1, wherein the clamp comprises a collet disposable over the implant and wherein the cooling mechanism is configured to fit over the collet and compress the collet against the implant.

15. The device of claim 1, wherein the clamp comprises an expandable member disposable within a recess formed in the implant and a tightening nut matable to the expandable member such that rotation of the nut relative to the expandable member causes a wedge portion of the nut to expand the expandable member into engagement with the recess.

* * * * *